(12) United States Patent
Ueda

(10) Patent No.: US 10,772,660 B2
(45) Date of Patent: Sep. 15, 2020

(54) MEDICAL PUNCTURE NEEDLE AND METHOD FOR MANUFACTURING PUNCTURE NEEDLE

(71) Applicant: Terumo Kabushiki Kaisha, Tokyo (JP)

(72) Inventor: Takehiko Ueda, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 80 days.

(21) Appl. No.: 15/883,674

(22) Filed: Jan. 30, 2018

(65) Prior Publication Data
US 2018/0146983 A1 May 31, 2018

Related U.S. Application Data

(63) Continuation of application No. PCT/JP2016/003398, filed on Jul. 20, 2016.

(30) Foreign Application Priority Data

Jul. 30, 2015 (JP) .................. 2015-151311

(51) Int. Cl.
*A61B 17/34* (2006.01)
*A61M 5/32* (2006.01)
(Continued)

(52) U.S. Cl.
CPC ......... *A61B 17/3421* (2013.01); *A61M 5/158* (2013.01); *A61M 5/32* (2013.01);
(Continued)

(58) Field of Classification Search
CPC ................ A61M 5/158; A61M 5/3286; A61M 2205/195; A61M 5/32; A61B 17/3421; A61B 2017/3454
See application file for complete search history.

(56) References Cited

U.S. PATENT DOCUMENTS

| 2,601,580 A | 6/1952 | Bronislowj |
| 3,071,135 A | 1/1963 | Baldwin et al. |
| (Continued) | | |

FOREIGN PATENT DOCUMENTS

| CN | 1140092 A | 1/1997 |
| DE | 2005 519 A1 | 10/1971 |
| (Continued) | | |

OTHER PUBLICATIONS

International Search Report Issued in International Patent Application No. PCT/JP2016/003398 dated Sep. 6, 2016.
(Continued)

*Primary Examiner* — Tiffany Legette
(74) *Attorney, Agent, or Firm* — Foley & Lardner LLP

(57) ABSTRACT

A medical puncture needle includes: a distal end portion including a needle point; and a rod-like main body portion continuous with the distal end portion, wherein: the distal end portion includes a blade surface, the blade surface includes: a first blade surface portion and a second blade surface portion on a front side of the distal end portion, the first and second blade surface portions intersecting each other at a ridgeline that forms a blade edge having the needle point at one end, and a third blade surface portion continuous with each of the first blade surface portion and the second blade surface portion on a main body portion side, and the third blade surface portion includes a protruding curved surface.

12 Claims, 17 Drawing Sheets

(51) Int. Cl.
*A61M 5/158* (2006.01)
*B24B 19/16* (2006.01)
*A61B 17/00* (2006.01)

(52) U.S. Cl.
CPC ............ *A61M 5/3286* (2013.01); *B24B 19/16* (2013.01); *A61B 2017/00526* (2013.01); *A61B 2017/3454* (2013.01); *A61M 2207/10* (2013.01)

(56) References Cited

U.S. PATENT DOCUMENTS

| | | | |
|---|---|---|---|
| 3,308,822 A | | 3/1967 | De Luca |
| 3,448,740 A | * | 6/1969 | Figge ............... A61M 5/3286 604/274 |
| 5,752,942 A | * | 5/1998 | Doyle ................ B24B 19/16 604/274 |
| 2005/0107751 A1 | * | 5/2005 | Yatabe ............... A61M 5/158 604/272 |

FOREIGN PATENT DOCUMENTS

| | | |
|---|---|---|
| DE | 10 2005 027 147 A1 | 12/2006 |
| EP | 0 739 640 A1 | 10/1996 |
| JP | S48-25998 B1 | 8/1973 |
| JP | H09-56815 A | 3/1997 |
| JP | H09-276403 A | 10/1997 |
| JP | 2000-262615 A | 9/2000 |
| JP | 2007-501062 A | 1/2007 |
| JP | 2012-115336 A | 6/2012 |
| JP | 2014-004249 A | 1/2014 |
| WO | WO-02/074367 A2 | 9/2002 |

OTHER PUBLICATIONS

Extended European Search Report issued in the corresponding European Patent Application Ser. No. 16830041.6, dated Jun. 26, 2019.

Japanese Patent Office, "Notice of Reasons for Refusal," issued in connection with Japanese Patent Application No. 2017-531009, dated Apr. 7, 2020.

The State Intellectual Property Office of the People's Republic of China, "Office Action," issued in connection with Chinese Patent Application No. 201680044415.6, dated Mar. 12, 2020.

* cited by examiner

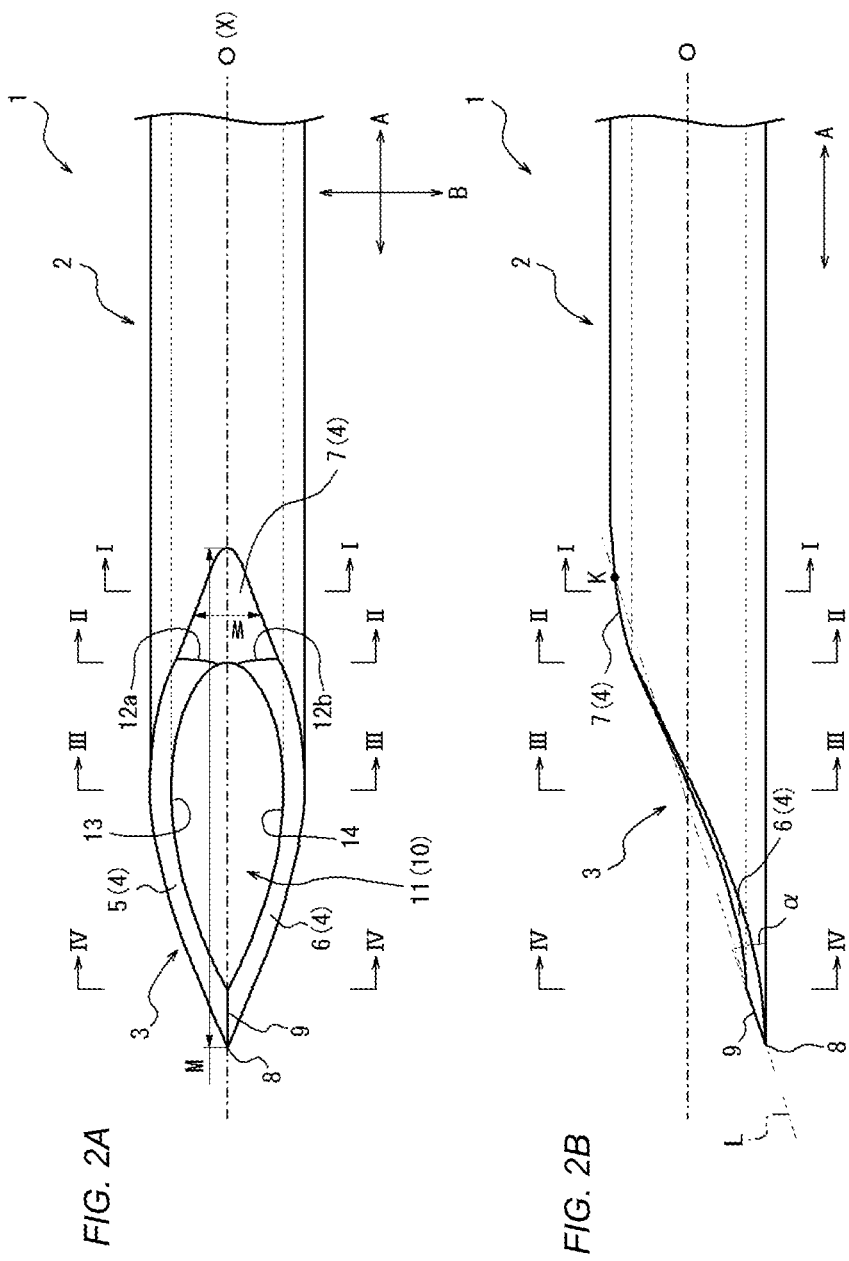

CROSS SECTION I-I

CROSS SECTION II-II

CROSS SECTION III-III

CROSS SECTION IV-IV

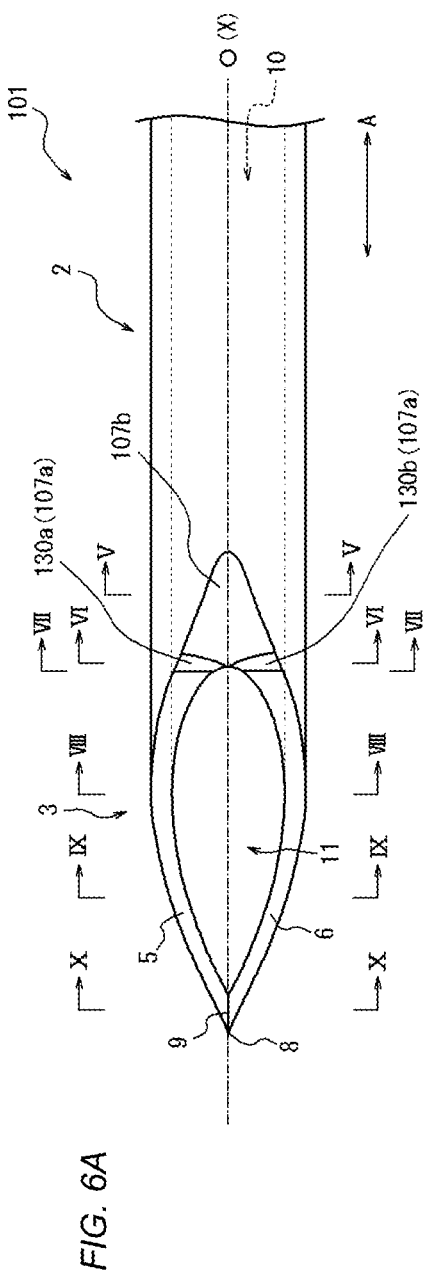
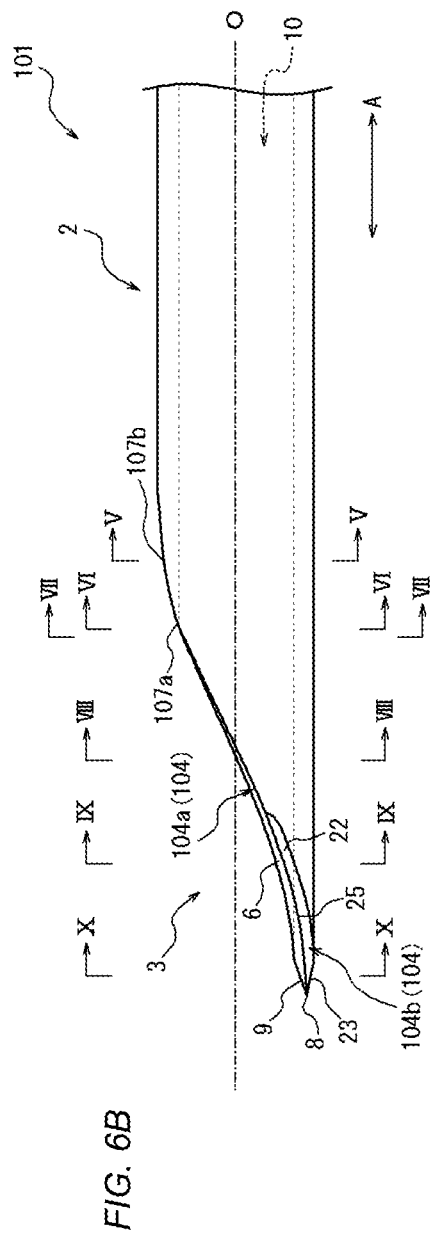

CROSS SECTION V-V

CROSS SECTION VI-VI

CROSS SECTION VII-VII

CROSS SECTION VIII-VIII

CROSS SECTION IX-IX

CROSS SECTION X-X

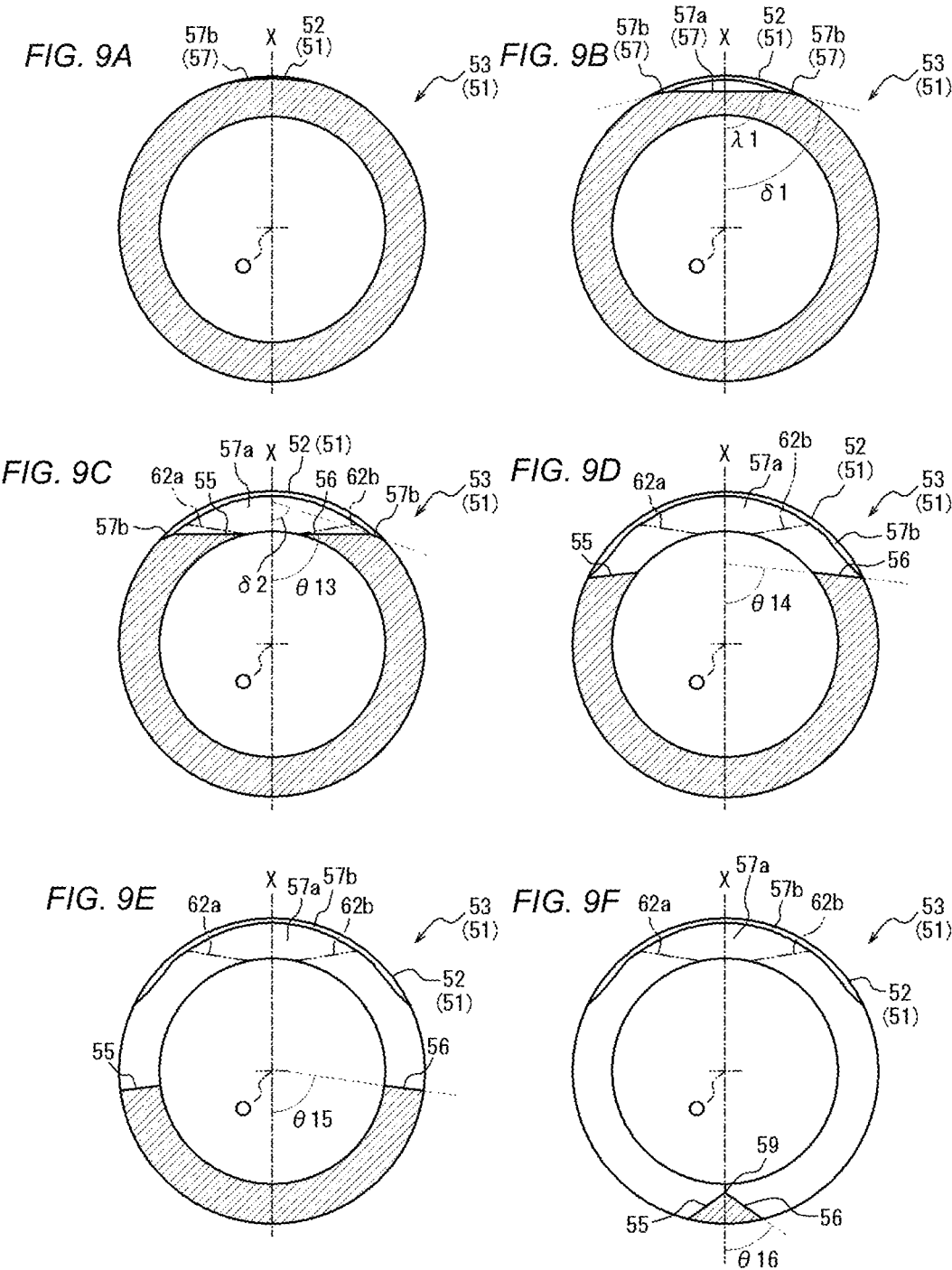

MEDICAL PUNCTURE NEEDLE AND METHOD FOR MANUFACTURING PUNCTURE NEEDLE

CROSS-REFERENCE TO RELATED APPLICATIONS

The present application is a bypass continuation of PCT Application No. PCT/JP2016/003398, filed on Jul. 20, 2016, which claims priority to Japanese Application No. 2015-151311, filed on Jul. 30, 2015, the contents of which are hereby incorporated by reference in their entireties.

BACKGROUND

The present disclosure relates to a medical puncture needle and a method for manufacturing the puncture needle.

Conventionally, there is a known medical puncture needle such as a blood collection needle or an indwelling needle for infusion, which includes a distal end portion including a plurality of blade surfaces having different angles with respect to the longitudinal direction of the puncture needle in order to alleviate pain when puncturing the human body with the puncture needle.

JP 2000-262615 A discloses an injection needle serving as such a puncture needle. The injection needle disclosed in JP 2000-262615 A is an injection needle including a tapered tip end portion formed by diagonally cutting out a cylindrical main body tip end portion from any one side. This injection needle includes a first inclined surface connected from an outer circumference of the cylindrical main body and formed at a predetermined angle with respect to the axial direction (longitudinal direction) of the main body, a second inclined surface connected to the first inclined surface and having an angle with respect to the axial direction of the main body greater than the first inclined surface, and a third inclined surface connected to the second inclined surface and to the blade tip and having an angle with respect to the axial direction of the main body greater than the second inclined surface.

SUMMARY

While it is possible to alleviate pain when the human body is punctured by the injection needle using a distal end portion having a blade surface connected to a plurality of inclined surfaces having different angles with respect to the longitudinal direction, as described as an injection needle in JP 2000-262615 A, a ridgeline is likely to be formed at a connecting portion between the first inclined surface and the outer circumference of the cylindrical main body as the main body portion because the first inclined surface of the blade surface is a plane, and there is a possibility that this ridgeline acts to increase penetration resistance during puncture using the injection needle, making it difficult to sufficiently alleviate the pain of the patient, or the like.

An object of certain embodiments of the present disclosure is to provide a medical puncture needle having a blade surface shape that is unlikely to form a ridgeline that acts to increase penetration resistance between the blade surface of the distal end portion and the main body portion, and a method for manufacturing the puncture needle.

According to one embodiment, a medical puncture needle includes a distal end portion including a needle point and a rod-like main body portion continuous with the distal end portion, in which the distal end portion includes a blade surface, the blade surface includes a first blade surface portion and a second blade surface portion intersecting each other to be a ridgeline to form a blade edge having the needle point as one end by the ridgeline and includes a third blade surface portion continuous with each of the first blade surface portion and the second blade surface portion on the main body portion side, and the third blade surface portion includes a protruding curved surface.

In one aspect, in a case where one virtual plane including a center axis of the main body portion is established, the protruding curved surface is constituted with a curved surface in which an angle with respect to the virtual plane in a cross section orthogonal to a center axis direction gradually decreases toward the needle point side in the center axis direction.

In one aspect, in a case where one virtual plane including a center axis of the main body portion is established, the protruding curved surface is configured such that an angle with respect to the virtual plane in a cross section orthogonal to a center axis direction is substantially constant.

In one aspect, in a case where one virtual plane including a center axis of the main body portion is established, at least one of the first blade surface portion and the second blade surface portion is constituted with a curved surface in which an angle with respect to the virtual plane in a cross section orthogonal to a center axis direction gradually decreases toward the needle point side in the center axis direction.

In one aspect, the blade surface includes a fourth blade surface portion formed on a back side of the first blade surface portion and includes a fifth blade surface portion formed on a back side of the second blade surface portion, and in a case where the blade edge is defined as a first blade edge, the fourth blade surface portion and the fifth blade surface portion intersect each other to be a ridgeline and form a second blade edge having the needle point as one end by the ridgeline.

In one aspect, the first blade surface portion and the fourth blade surface portion intersect each other to be a ridgeline and form a third blade edge having the needle point as one end by the ridgeline and that the second blade surface portion and the fifth blade surface portion intersect each other to be a ridgeline and form a fourth blade edge having the needle point as one end by the ridgeline.

In one aspect, at least one of the fourth blade surface portion and the fifth blade surface portion is constituted with a curved surface in which an angle with respect to the virtual plane in a cross section orthogonal to the center axis direction gradually increases toward the needle point side in the center axis direction.

In one aspect, the virtual plane can be established in one plane including the center axis and the needle point.

In one aspect, a straight line connecting the needle point with a point on the third blade surface portion in the one plane is inclined at an angle of more than 12 degrees and 18 degrees or less with respect to the center axis.

According to another embodiment, a medical puncture needle includes a main body portion having a flat cross sectional outline defined by a major axis and a minor axis, a distal end portion continuous with the main body portion and including a needle point, in which the distal end portion includes a blade surface, the blade surface includes a first blade surface portion and a second blade surface portion intersecting each other to be a ridgeline to form a blade edge having the needle point as one end by the ridgeline, and the first blade surface portion and the second blade surface portion form a curved surface.

According to another embodiment, a method for manufacturing a medical puncture needle is a method of forming a blade surface on one end portion of a rod-like member by bringing the one end portion into sliding contact with a grinding surface of a rotating grindstone, the method for manufacturing a medical puncture needle including forming a blade surface portion having a curved surface by bringing the one end portion into sliding contact with the grinding surface while varying a tilt angle of a center axis with respect to the grinding surface while causing the rod-like member to pivot about the center axis of the rod-like member.

According to certain embodiments, it is possible to provide a medical puncture needle having a blade surface shape that is unlikely to form a ridgeline that acts to increase penetration resistance between the blade surface of the distal end portion and the main body portion, and a method for manufacturing the puncture needle.

BRIEF DESCRIPTION OF THE DRAWINGS

FIGS. 1A-1D are diagrams illustrating a puncture needle according to an embodiment of the present invention, in which FIG. 1A is a plan view of a front side, FIG. 1B is a side view, FIG. 1C is a plan view of a back side, and FIG. 1D is a perspective view.

FIG. 2A is an enlarged view of a distal end portion illustrated in FIG. 1A, and FIG. 2B is an enlarged view of a distal end portion illustrated in FIG. 1B.

FIGS. 5A-5D are diagrams illustrating a puncture needle according to an embodiment of the present invention, in which FIG. 5A is a plan view of a front side, FIG. 5B is a side view, FIG. 5C is a plan view of a back side, and FIG. 5D is a perspective view.

FIG. 6A is an enlarged view of a distal end portion illustrated in FIG. 5A, and FIG. 6B is an enlarged view of a distal end portion illustrated in FIG. 5B.

FIGS. 8A and 8B are diagrams illustrating a puncture needle according to an embodiment of the present invention, in which FIG. 8A is a perspective view, and FIG. 8B is a plan view of a front side in the vicinity of the distal end portion.

FIGS. 9A, 9B, 9C, 9D, 9E and 9F are cross sectional views taken along lines XI-XI, XII-XII, XIII-XIII, XIV-XIV, XV-XV, and XVI-XVI, respectively, in FIG. 8B.

FIGS. 15A-15C are diagrams illustrating an example of the puncture needle according to one embodiment, in which FIG. 15A is a perspective view in the vicinity of the distal end portion, FIG. 15B is a plan view of a front side in the vicinity of the distal end portion, and FIG. 15C is a side view in the vicinity of the distal end portion.

DETAILED DESCRIPTION

Figure 1A:
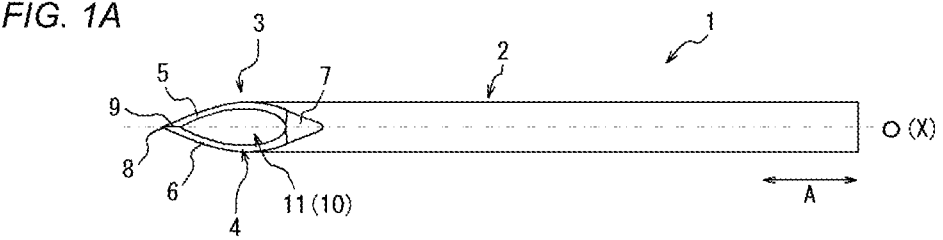

Hereinafter, a medical puncture needle and a method for manufacturing the puncture needle according to embodiments of the present invention will be described with reference to FIGS. 1 to 17. In the drawings, common members are denoted by the same reference numerals.

First Embodiment

Figure 1B:
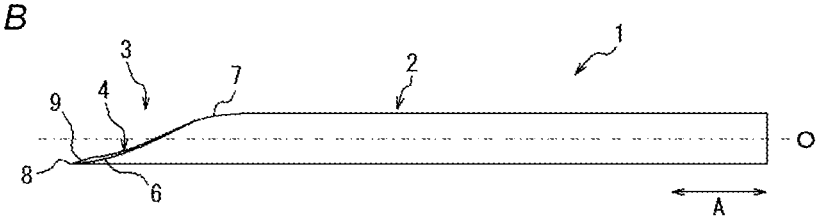
Figure 1C:
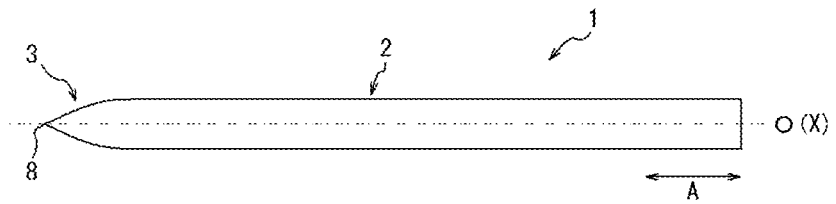
Figure 1D:
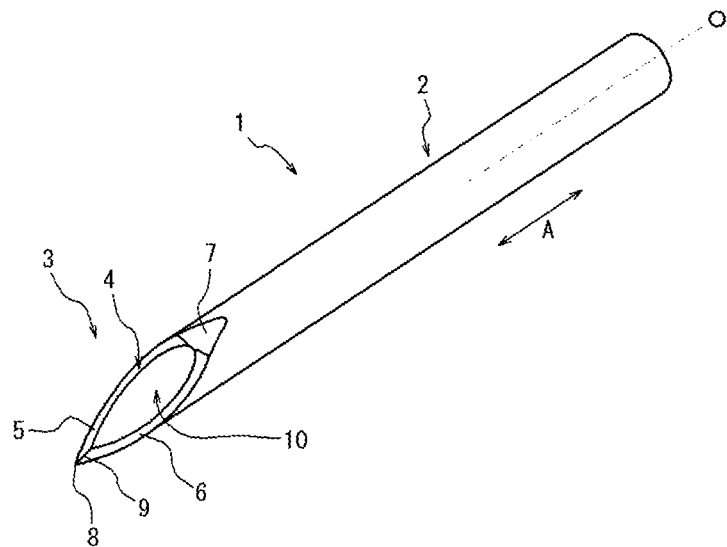

First, a puncture needle 1 as one embodiment of a medical puncture needle according to the present invention will be described. FIGS. 1A-1D are diagrams illustrating the puncture needle 1. Specifically, FIG. 1A is a plan view of a front side of the puncture needle 1, FIG. 1B is a side view of the puncture needle 1, FIG. 1 C is a plan view of a back side of the puncture needle 1. FIG. 1D is a perspective view of the puncture needle 1.

As illustrated in FIGS. 1A to 1D, the puncture needle 1 includes a main body portion 2 and a distal end portion 3, and sections a hollow portion 10 communicating from the main body portion 2 to the distal end portion 3.

The main body portion 2 is a hollow rod-like body, namely, a tubular pipe body continuous with the distal end portion 3. More specifically, the main body portion 2 according to the present embodiment is a pipe body continuous with the distal end portion 3 and having a substantially circular cross sectional outline. Here, the "cross section" of the "cross sectional outline" represents a transverse cross section orthogonal to a center axis O of the main body portion 2.

As illustrated in FIGS. 1A to 1D, the distal end portion 3 includes a blade surface 4, and the blade surface 4 includes a first blade surface portion 5, a second blade surface portion 6 and a third blade surface portion 7, each formed with a curved surface. The first blade surface portion 5 and the second blade surface portion 6 intersect each other to be a ridgeline and form a blade edge 9 having a needle point 8 as one end by the ridgeline. Note that the "needle point" represents the distal end of the puncture needle 1 in an axial direction A of the center axis O of the main body portion 2 (hereinafter simply referred to as "center axis direction A").

The third blade surface portion 7 is continuous with the outer circumferential surface of the main body portion 2 on the main body portion 2 side in the center axis direction A and continuous with the first blade surface portion 5 and the second blade surface portion 6 on the needle point 8 side in the center axis direction A.

More specifically, each of the first blade surface portion 5 and the second blade surface portion 6 is continuous with the third blade surface portion 7 on the main body portion 2 side in the center axis direction A, and intersect each other on the needle point 8 side to form a ridgeline, namely, form the blade edge 9. Moreover, the first blade surface portion 5 and the second blade surface portion 6 in the present embodiment section an opening 11, that is, one end of the hollow portion 10 on the distal end portion 3 side.

As can be seen from the side view in FIG. 1B, the angle of the second blade surface portion 6 in the cross section orthogonal to the center axis direction A changes depending on the position in the center axis direction A. Specifically, in FIG. 1B, while merely an outer edge of the second blade surface portion 6 can be visually recognized at a position where the second blade surface portion 6 and the third blade surface portion 7 are continuous with each other in the center axis direction A, the second blade surface portion 6 can be visually recognized at a position where the blade edge 9 is formed in the center axis direction A. That is, the second blade surface portion 6 is constituted with a curved surface, similar to a helical surface, for example, extending in a twisted manner from the position continuous with the third blade surface portion 7 toward the needle point 8 in the center axis direction A. Similarly to the second blade surface portion 6, the first blade surface portion 5 is also constituted with a curved surface extending in a twisted manner from the position continuous with the third blade surface portion 7 toward the needle point 8 in the center axis direction A. Note that the directions of twisting of the first blade surface portion 5 and the second blade surface portion 6 toward the needle point 8 side are opposite to each other.

In other words, in a case where one virtual plane including the center axis O of the main body portion 2 is established, each of the first blade surface portion 5 and the second blade surface portion 6 is constituted with a curved surface in which an angle θ with respect to the one virtual plane in a cross section orthogonal to the center axis direction A gradually decreases toward the needle point 8 side in the center axis direction A. In short, the puncture needle 1 according to the present embodiment is a puncture needle capable of defining such one virtual plane.

Here, the puncture needle 1 according to the present embodiment includes one plane that can be defined as the above-described "virtual plane". Specifically, the puncture needle 1 according to the present embodiment enables the above-described "virtual plane" to be established in a plane including the center axis O and the needle point 8 (hereinafter referred to as a "center plane X"), and is configured such that each of the first blade surface portion 5 and the second blade surface portion 6 is constituted with a curved surface in which the angle θ with respect to the center plane X in a cross section orthogonal to the center axis direction A gradually decreases toward the needle point 8 side in the center axis direction A. Note that the center plane X according to the present embodiment is a plane including not solely the needle point 8 but also the blade edge 9.

While the puncture needle 1 according to the present embodiment is configured such that both the first blade surface portion 5 and the second blade surface portion 6 are constituted with curved surfaces in which the angle θ with respect to the center plane X in a cross section orthogonal to the center axis direction A gradually decreases toward the needle point 8 side in the center axis direction A, it is also allowable to configure such that any one of the first blade surface portion 5 and the second blade surface portion 6 is constituted with such a curved surface while the other is constituted with a plane or a curved surface having another surface shape. Moreover, both the first blade surface portion 5 and the second blade surface portion 6 may be constituted with planes or curved surfaces each having another surface shape. Still, with a configuration of the present embodiment in which both the first blade surface portion 5 and the second blade surface portion 6 are constituted with curved surfaces in which the angle θ with respect to the center plane X in a cross section orthogonal to the center axis direction A gradually decreases toward the needle point 8 side in the center axis direction A, it is possible to facilitate achieving the blade surface 4 that is unlikely to form a ridgeline (junction) having a possibility of becoming penetration resistance, between the first blade surface portion 5/second blade surface portion 6 and the third blade surface portion 7.

Details of the curved surface shapes of the first blade surface portion 5 and the second blade surface portion 6 will be described below (refer to FIGS. 3A-3D or the like).

The third blade surface portion 7 has a protruding curved surface. Specifically, the third blade surface portion 7 according to the present embodiment is constituted with solely a protruding curved surface continuous with the first blade surface portion 5 and the second blade surface portion 6. More specifically, the third blade surface portion 7 is constituted with a protruding curved surface in which the angle θ with respect to the center plane X in the cross section orthogonal to the center axis direction A is substantially constant regardless of the position in the center axis direction A.

Herein, the "distal end portion" in the present application represents a portion in which a blade surface is formed in the center axis direction A of the puncture needle, while the "main body portion" represents a portion in which the blade surface is not formed on the puncture needle, in the center axis direction A. Accordingly, in the present embodiment, the distal end portion 3 corresponds to a portion in which the first blade surface portion 5, the second blade surface portion 6, and the third blade surface portion 7 are formed in the center axis direction A on the tubular member as an integral hollow rod-like member constituting the puncture needle 1. In the present embodiment, the main body portion 2 corresponds to a portion having a substantially circular cross sectional outline, in which the first blade surface portion 5, the second blade surface portion 6, and the third blade surface portion 7 are not formed in the center axis direction A on the integral tubular member constituting the puncture needle 1.

Examples of materials applicable as the puncture needle 1 in the present embodiment include a metal material such as stainless steel, aluminum or an aluminum alloy, titanium or a titanium alloy.

Hereinafter, individual configurations and characteristic portions according to the present embodiment will be described in detail.

[Main Body Portion 2]

The main body portion 2 according to the present embodiment is a pipe body having a uniform inner diameter of the inner circumferential surface and a uniform outer diameter of the outer circumferential surface in the center axis direction A, with an end portion on the opposite side of the distal end portion 3 side in the center axis direction A being connected to a medical instrument such as a syringe via a needle hub, or the like.

Note that while the present embodiment is a case where the inner circumferential surface (the inner circumferential surface of the main body portion 2 and the inner circumferential surface of the distal end portion 3) of the tubular member constituting the entire puncture needle 1 sections the hollow portion 10, with the inner diameter of the inner circumferential surface and the outer diameter of the outer circumferential surface of the tubular member being uniform in the center axis direction A, the configuration is not limited to this configuration. For example, alternatively, it is allowable to configure such that the inner diameter of the inner circumferential surface of the tubular member and the outer diameter of the outer circumferential surface of the tubular member gradually decrease toward the distal end portion 3 side in the center axis direction A. Still alternatively, for example, it is also possible to configure such that the outer diameter of the tubular member is tapered to gradually decrease toward the distal end portion 3 side in the center axis direction A and that the inner diameter of the tubular member is uniform in the center axis direction A. Furthermore, various configurations can be adopted for the inner and outer diameters of the tubular member constituting the puncture needle 1 in accordance with the usage of the puncture needle 1, including an exemplary case of providing a portion in which the inner diameter gradually decreases or gradually increases toward the distal end portion 3 side in the center axis direction A, in a portion of the region of the center axis direction A.

[First Blade Surface Portion 5 and Second Blade Surface Portion 6 of the Distal End Portion 3]

FIGS. 2A and 2B are enlarged views of the distal end portion 3 illustrated in FIGS. 1A and 1B, respectively. FIGS. 3A, 3B, 3C, and 3D are a cross sectional views taken along lines I-I, II-II, III-III and IV-IV, respectively, in FIGS. 2A and 2B.

As illustrated in FIG. 2A, each of the first blade surface portion 5 and the second blade surface portion 6 is continuous with the third blade surface portion 7 on the main body portion 2 side in the center axis direction A. More specifically, each of the first blade surface portion 5 and the second blade surface portion 6 is continuous with the third blade surface portion 7 on either side sandwiching the center plane X.

Figure 3A:
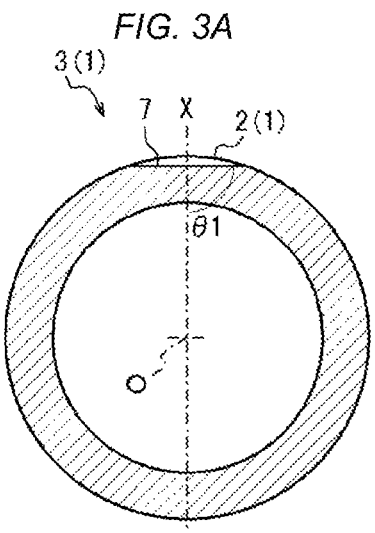
FIG. 3A is a cross sectional view taken along line I-I in FIGS. 2A and 2B.
Figure 3B:
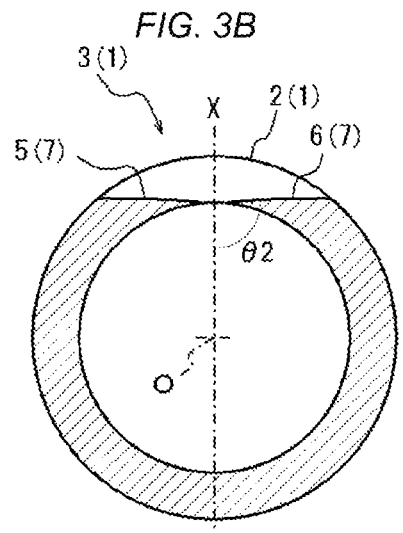
FIG. 3B is a cross sectional view taken along line II-II in FIGS. 2A and 2B.

FIG. 3B is a cross section taken along line II-II in FIGS. 2A and 2B, that is, a cross section orthogonal to the center axis direction A at a position where the first blade surface portion 5 and the second blade surface portion 6 are connected to the third blade surface portion 7 in the center axis direction A. As illustrated in FIG. 3B, an angle θ2 of each of the first blade surface portion 5 and the second blade surface portion 6 in cross section II-II in FIGS. 2A and 2B with respect to the center plane X is about 90 degrees. In other words, in cross section II-II in FIGS. 2A and 2B, each of the first blade surface portion 5 and the second blade surface portion 6 extends linearly in a direction orthogonal to the center plane X.

Note that while each of the first blade surface portion 5 and the second blade surface portion 6 illustrated in FIG. 3B is represented by a line substantially orthogonal to the center plane X, this line substantially matches boundary lines 12a and 12b representing boundaries between the first blade surface portion 5/second blade surface portion 6, and the third blade surface portion 7. Specifically, as illustrated in FIG. 2A, a portion toward the needle point 8 side from the boundary line 12a is the first blade surface portion 5, and a portion toward the main body portion 2 side from the boundary line 12a is the third blade surface portion 7. Similarly, a portion toward the needle point 8 side from the boundary line 12b is the second blade surface portion 6, and a portion toward the main body portion 2 side from the boundary line 12b is the third blade surface portion 7. Note that in the present embodiment, the boundary lines 12a between the first blade surface portion 5 and the third blade surface portion 7 and the boundary lines 12b between the second blade surface portion 6 and the third blade surface portion 7 are smoothly continuous with each other so as not to form a ridgeline (junction), and thus, the boundary lines 12a and 12b illustrated in FIG. 2A are not the line representing the ridgelines but the lines simply indicating the boundaries. Still, it is also allowable to form the boundary lines 12a and 12b by ridgelines that would not significantly increase the penetration resistance.

Figure 3C:
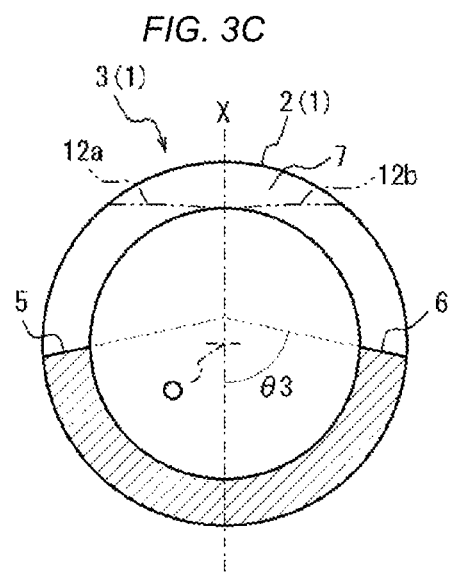
FIG. 3C is a cross sectional view taken along line III-III in FIGS. 2A and 2B.

FIG. 3C illustrates a cross section taken along line III-III in FIGS. 2A and 2B, that is, a cross section orthogonal to the center axis direction A at a position of the opening 11 in the center axis direction A. As illustrated in FIG. 3C, an angle θ3 of each of the first blade surface portion 5 and the second blade surface portion 6 in cross section III-III in FIGS. 2A and 2B with respect to the center plane X is an acute angle smaller than the angle θ2. In FIG. 3C, the above-described boundary lines 12a and 12b are indicated by two-dot chain lines.

Figure 3D:
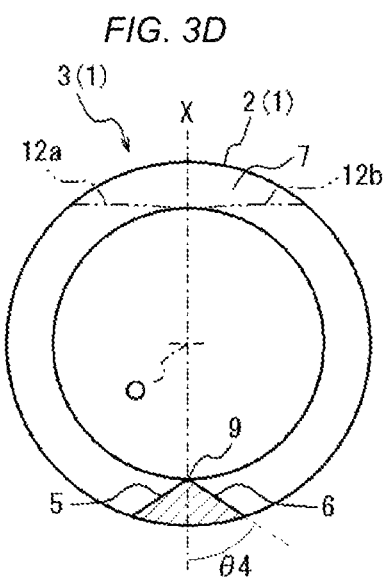
FIG. 3D is a cross sectional view taken along line IV-IV in FIGS. 2A and 2B.

FIG. 3D illustrates a cross section taken along line IV-IV in FIGS. 2A and 2B, that is, a cross section orthogonal to the center axis direction A at a position where the blade edge 9 is formed in the center axis direction A. As illustrated in FIG. 3D, an angle θ4 of each of the first blade surface portion 5 and the second blade surface portion 6 in cross section IV-IV in FIGS. 2A and 2B with respect to the center plane X is an acute angle smaller than the angle θ2 and smaller than the angle θ3. In FIG. 3D, the boundary lines 12a and 12b are also indicated by two-dot chain lines.

In this manner, the first blade surface portion 5 and the second blade surface portion 6 are straight lines in a cross sectional views orthogonal to the center axis direction A (refer to FIGS. 3B to 3D), and the angle θ of each of the first blade surface portion 5 and the second blade surface portion 6 according to the present embodiment with respect to the center plane X in the cross section orthogonal to the center axis direction A gradually decreases toward the needle point 8 side (at a closer position to the needle point 8) in the center axis direction A. Note that while FIGS. 3B to 3D illustrate the angles θ2 to θ4 of the second blade surface portion 6 with respect to the center plane X respectively, the angles of the first blade surface portion 5 with respect to the center plane X are also the same as the angles θ2 to θ4 of the second blade surface portion 6. The three cross sections in FIGS. 3B to 3D are merely examples to illustrate the size relationship between the angles θ2, θ3, and θ4, and the size relationship of the above-described angles θ is not limited to these three cross sections.

Also note that as illustrated in FIGS. 3B to 3D, while the second blade surface portion 6 according to the present embodiment is a straight line in a cross sectional view orthogonal to the center axis direction A, the configuration is not limited to this particular configuration. Instead, for example, it is possible to configure such that the cross sectional view of the second blade surface portion, orthogonal to the center axis direction A, is formed with an arcuate curved line, and that the cross sectional view is formed with a straight line with an arcuate curved line continuous with this straight line. This also applies to the first blade surface portion in a similar manner. In this case, the angle θ of the first blade surface portion and the second blade surface portion indicates the angle formed by a straight line passing through an inner edge and an outer edge of each of the first blade surface portion and the second blade surface portion in the cross section orthogonal to the center axis direction A, and by one established virtual plane (center plane X in the present embodiment).

[Blade Edge 9 of Distal End Portion 3]

As described above, the blade edge 9 is formed by a ridgeline on which the first blade surface portion 5 and the second blade surface portion 6 intersect each other. As described above, the blade edge 9 according to the present embodiment extends in the center plane X, and thus, the needle point 8 as one end of the blade edge 9 is also located in the center plane X. That is, the puncture needle 1 according to the present embodiment is a hollow needle having a symmetrical configuration with respect to the center plane X.

When the distal end of the puncture needle 1 is sharpened so as to provide the blade edge 9 as illustrated in the present embodiment, the blade edge 9, an outer edge of the first blade surface portion 5 and an outer edge of the second blade surface portion 6 in the vicinity of the blade edge 9 act as a cutting edge for incising the skin when the puncture needle 1 punctures the human body, making it possible to reduce the resistance applied to the skin at the time of puncture. Therefore, it is possible to alleviate the pain sensed by a patient, or the like, to whom the puncture needle 1 is applied in puncture.

As described above, the angle θ (refer to FIGS. 3B to 3D) of each of the first blade surface portion 5 and the second blade surface portion 6 decreases toward the needle point 8 in the center axis direction A. This also applies in a similar manner even in a region where the blade edge 9 is located in the center axis direction A. That is, the angle θ gradually decreases from one end of the blade edge 9 on the main body portion 2 side in the center axis direction A toward the needle point 8 along the blade edge 9. With this configuration, the puncture needle 1 according to the present embodiment can be formed to be sharper in the vicinity of the needle point 8 as compared with a configuration in which the angle θ is uniform in the region where the blade edge 9 extends in the center axis direction A, making it possible to further alleviate the pain of the patient, or the like, at the time of puncture with the puncture needle 1. Note that it is allowable to configure in one aspect such that the angle θ gradually decreases partially. For example, such an aspect is achieved with a configuration including two portions in which the angle θ of the first blade surface portion and the second blade surface portion gradually decreases and a portion therebetween having a constant angle θ, continuous with the two portions.

[Third Blade Surface Portion 7 of the Distal End Portion 3]

As illustrated in FIGS. 2A and 2B, the third blade surface portion 7 is a curved surface inclined with respect to the center axis direction A. The main body portion 2 side of the third blade surface portion 7 is continuous with the outer circumferential surface of the main body portion 2, while the needle point 8 side of the third blade surface portion 7 is continuous with the first blade surface portion 5 and the second blade surface portion 6.

The third blade surface portion 7 is a protruding curved surface inclined so as to be closer to the center axis O toward the needle point 8 in the center axis direction A, in a side view in FIG. 2B. Moreover, the third blade surface portion 7 according to the present embodiment has the angle θ with respect to the center plane X in the cross section orthogonal to the center axis direction A being substantially constant regardless of the position in the center axis direction A. Specifically, as illustrated in FIG. 3A, the angle θ1 of the third blade surface portion 7 according to the present embodiment with respect to the center plane X in cross section I-I in FIGS. 2A and 2B is about 90 degrees, and the angle θ of the third blade surface portion 7 according to the present embodiment with respect to the center plane X of the third blade surface portion 7 is about 90 degrees regardless of the position in the center axis direction A, namely, any position other than on cross section I-I in FIGS. 2A and 2B. In other words, as illustrated in FIG. 3A, the third blade surface portion 7 according to the present embodiment extends linearly in a direction orthogonal to the center plane X, in the cross section orthogonal to the center axis direction A.

The third blade surface portion 7 is inclined so as to gradually come closer to the center axis O toward the needle point 8 side in the center axis direction A, and the inclination angle of the third blade surface portion 7 with respect to the center axis direction A is greater than the inclination angle of an outer wall of the main body portion 2 with respect to the center axis direction A in the cross section including the entire center axis O. Since the third blade surface portion 7 is a curved surface, the "inclination angle of the third blade surface portion with respect to the center axis direction" as described herein corresponds to the angle formed by a tangent line at an arbitrary point on the third blade surface portion and the center axis, on a cross section including the entire center axis and passing on the third blade surface portion.

The present embodiment has a configuration in which the outer diameter of the tubular member constituting the puncture needle 1 is uniform in the center axis direction A, and the outer wall of the tubular member extends in the center axis direction A when viewed in a cross section including the entire center axis O. Accordingly, when the third blade surface portion 7 is inclined with respect to the center axis direction A, the inclination angle of the third blade surface portion 7 is greater than the inclination angle of the outer wall of the main body portion 2. In a case, however, where the tubular member constituting the puncture needle 1 is configured to have the outer diameter that gradually decreases or gradually increases toward the distal end portion 3 side in the center axis direction A, it is preferable that the third blade surface portion 7 is not merely inclined with respect to the center axis direction A, but also inclined with respect to the outer wall of the main body portion 2 in the cross section including the entire center axis O.

As described above, the angle θ of the third blade surface portion 7 according to the present embodiment with respect to the center plane X is about 90 degrees regardless of the position in the center axis direction A. Moreover, the first blade surface portion 5 and the second blade surface portion 6 are smoothly continuous with the third blade surface portion 7 without forming a ridgeline with the third blade surface portion 7 at the boundary lines 12a and 12b described above (refer to FIG. 3B).

Moreover, as illustrated in FIG. 2A, the third blade surface portion 7 is a curved surface having a width W in an orthogonal direction B orthogonal to the center axis direction A toward the needle point 8 side in the center axis direction A in a plan view of the front side. Moreover, the amount of increase in the width W (amount of change in the width W per unit length in the center axis direction A) is greater toward the needle point 8 side in the center axis direction A.

[Blade Surface 4 Including First Blade Surface Portion 5, Second Blade Surface Portion 6 and Third Blade Surface Portion 7]

The blade surface 4 includes the above-described first blade surface portion 5, second blade surface portion 6, and third blade surface portion 7. As described above, each of the first blade surface portion 5 and the second blade surface portion 6 of the blade surface 4 is constituted with a curved surface in which the angle θ with respect to the center plane X in a cross section orthogonal to the center axis direction A gradually decreases toward the needle point 8 side in the center axis direction A. By forming the first blade surface portion 5 and the second blade surface portion 6 in such shapes, the facing direction of the first blade surface portion 5 and the second blade surface portion 6 is changed from the position of cross section II-II toward the needle point 8 side. This results in achieving formation of the blade edge 9 on which the first blade surface portion 5 and the second blade surface portion 6 intersect each other at a position more toward the needle point 8 side than the opening 11 in the center axis direction A, without forming a ridgeline of a level that has a possibility of becoming penetration resistance at a connecting position with the third blade surface portion 7, or merely having a ridgeline of a level that would not be a significant penetration resistance formed at the connecting position with the third blade surface portion 7 (refer to FIGS. 3A to 3D).

Figure 14:
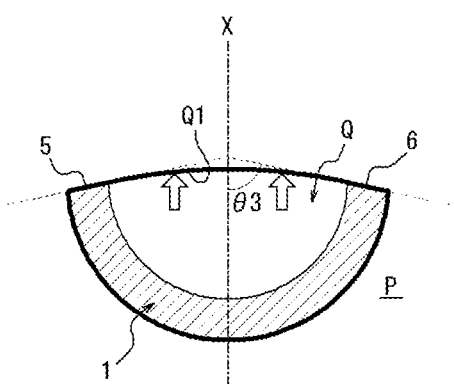
FIG. 14 is a schematic diagram illustrating a state of an incision when puncturing the body surface into the body with the puncture needle illustrated in FIGS. 1A-1D.

FIG. 14 is a schematic diagram illustrating a state of a moment when the cross section of the puncture needle 1 illustrated in FIG. 3C passes through a body surface P when the puncture is performed with the puncture needle 1 from the body surface P into the body. As illustrated in FIG. 14, the angle θ3 of the first blade surface portion 5 and the second blade surface portion 6 with respect to the center plane X is an acute angle smaller than 90 degrees. With this configuration, when puncturing is performed with the puncture needle 1 from the body surface into the body, an edge portion Q1 of an incision Q formed on the body surface is pressed by the first blade surface portion 5 and the second blade surface portion 6 in a direction of pushing the incision Q apart (refer to a hollow arrow in FIG. 14) The angle θ of the first blade surface portion 5 and the second blade surface portion 6 with respect to the center plane X is an acute angle smaller than 90 degrees, not being limited to the cross section illustrated in FIG. 3C. Accordingly, the edge portion Q1 of the incision Q is pressed in a direction of pushing the incision Q apart while the first blade surface portion 5 and the second blade surface portion 6 pass through the body surface P. With this configuration, it is possible to suppress a situation in which the edge portion Q1 of the incision Q is pushed into the body together with the first blade surface portion 5 and the second blade surface portion 6 when the first blade surface portion 5 and the second blade surface portion 6 pass through the body surface P. In particular, since the connecting position between the first blade surface portion 5/second blade surface portion 6 and the third blade surface portion 7 is more toward the main body portion 2 side from the position where an inner edge 13 and an inner edge 14 become parallel to the center axis direction A, the edge portion Q1 of the incision Q is unlikely to be pushed into the body when a portion in the vicinity of main body portion 2-side (refer to FIGS. 1A-1D, or the like) edge portion of the opening 11 (refer to FIGS. 1A-1D, or the like) passes through the body surface P. Moreover, each of the first blade surface portion 5 and the second blade surface portion 6 is formed with a curved surface in which the inclination angle with respect to the plane orthogonal to the center plane X gradually increases toward the main body portion 2 side. Accordingly, the edge portion Q1 of the incision Q is pressed in a direction of pushing the incision Q apart while the first blade surface portion 5 and the second blade surface portion 6 pass through the body surface P. With this configuration, it is also possible to suppress the situation in which the edge portion Q1 of the incision Q is pushed into the body together with the first blade surface portion 5 and the second blade surface portion 6 when the first blade surface portion 5 and the second blade surface portion 6 pass on the body surface P. This makes it possible to suppress an increase in penetration resistance of the puncture needle 1 and to alleviate the risk of infection due to bacteria, or the like, on the body surface P.

Furthermore, as described below, each of the first blade surface portion 5 and the second blade surface portion 6 of the blade surface 4 is constituted with a curved surface in which the angle θ with respect to the center plane X in a cross section orthogonal to the center axis direction A gradually decreases toward the needle point 8 side in the center axis direction A. Moreover, the first blade surface portion 5 and the second blade surface portion 6 intersect each other at a position more toward the needle point 8 side from the opening 11 and form the blade edge 9. With this configuration, it is possible to set a blade tip angle α of the blade edge 9 (refer to FIG. 2B) to be smaller than the blade tip angle α of a case where the blade edge is formed by the ridgeline on which the two planar blade surface portions intersect each other. That is, the blade tip can be thinned. This makes it possible to reduce the penetration resistance in the vicinity of the needle point 8 when puncturing is performed with the puncture needle 1 into the human body. Note that the blade tip angle α represents an angle at which the blade edge crosses the back surface of the blade edge at the needle point in a side view (refer to FIG. 2B) of the puncture needle.

In particular, the puncture needle 1 according to the present embodiment is configured such that a straight line L (two-dot chain line in FIG. 2B) connecting the needle point 8 with a point K on the third blade surface portion 7 is inclined at an angle greater than 12 degrees and 18 degrees or less with respect to the center axis O, in the center plane X as one virtual plane. The point K on the third blade surface portion 7 on which the straight line L passes is an arbitrary point on the third blade surface portion 7 in the center plane X. With such a configuration, it is possible to form a blade surface length M of the blade surface 4 in the center axis direction A (length from the needle point 8 to one end on the main body portion 2 side of the third blade surface portion 7 in the center axis direction A) to be a length shorter than the blade surface length of a "regular bevel" (puncture needle with a blade surface formed solely by one inclined surface having an inclination angle of 12 degrees with respect to the center axis) mainly used for intramuscular injection, or the like, and it is possible to form the blade surface length M to be a blade surface length of a similar level of the blade surface length of a "regular bevel" (puncture needle with a blade surface formed solely by one inclined surface having an inclination angle of 18 degrees with respect to the center axis) mainly used for intravenous injection, or the like, while forming the blade tip angle α to be an angle of a level similar to the angle of the "regular bevel", or less. In short, it is possible to achieve the puncture needle 1 having a short blade surface length that is unlikely to induce penetration of a vessel such as a vein while being capable of reducing the penetration resistance in the vicinity of the needle point 8 and capable of easily obtaining the vessel. Moreover, achievement of reduction of the penetration resistance in the vicinity of the needle point 8 also leads to a decreased amount of change in the penetration resistance, making it possible to also decrease the amount of change in the force applied by the medical staff in the puncture direction at the time of puncturing. This leads to achievement of the puncture needle 1 the medical staff can easily operate at the time of puncturing.

While the blade tip angle α of the blade edge 9 can be reduced with the configuration in which the first blade surface portion 5 and the second blade surface portion 6 are constituted with curved surfaces in which the angle θ with respect to the center plane X in a cross section orthogonal to the center axis direction A gradually decreases toward the needle point 8 side in the center axis direction A as described above, this configuration is likely to form the first blade surface portion 5 and the second blade surface portion 6 to be a recessed shape in a side view as illustrated in FIG. 2B. Forming the first blade surface portion 5 and the second blade surface portion 6 in a recessed shape in a side view might lead to easy formation of a ridgeline to be a penetration resistance at a position of one end of the first blade surface portion 5 and the second blade surface portion 6 on the main body portion 2 side. This might increase the penetration resistance at the position of one end of the first blade surface portion 5 and the second blade surface portion 6 on the main body portion 2 side even in a case where reduction in penetration resistance in the vicinity of the needle point 8 is achieved.

Fortunately however, by configuring the third blade surface portion 7 of the blade surface 4 to have a protruding curved surface (in the case of the present embodiment, the third blade surface portion 7 is constituted with a protruding curved surface alone), the ridgeline having a possibility of becoming penetration resistance is not likely to be formed at the position of one end of the first blade surface portion 5 and the second blade surface portion 6 on the main body portion 2 side, that is, the position of the boundary lines 12a and 12b between the first blade surface portion 5/second blade surface portion 6 and the third blade surface portion 7 even in a case where the blade edge 9 has a small blade tip angle α. With this configuration, it is possible to achieve the puncture needle 1 in which the penetration resistance at the position of one end of the first blade surface portion 5 and the second blade surface portion 6 on the main body portion 2 side is unlikely to increase, with the blade tip angle α of the blade edge 9 being small.

Moreover, since the third blade surface portion 7 has a protruding curved surface, it is possible to achieve relatively smooth connection also at a boundary between the third blade surface portion 7 and the outer surface of the main body portion 2 in the center axis direction A, so as to be advantageous for reducing penetration resistance.

In this manner, according to the present embodiment, it is possible to achieve the puncture needle 1 having the blade surface 4 with a small blade tip angle α, unlikely to form a ridgeline (junction) having a possibility of becoming resistance and can reduce the penetration resistance in the vicinity of the needle point 8. This makes it possible, in puncturing the human body, to alleviate the pain sensed by a patient, or the like, punctured, and by forming a thin blade tip having a small blade tip angle α, it is possible to prevent a failure in obtaining the vessel at the time of puncture into the vessel, making it easier to obtain the vessel.

It is preferable that the angular change amount of the angle θ of each of the first blade surface portion 5 and the second blade surface portion 6 per unit length in the center axis direction A is constant. This configuration allows each of the first blade surface portion 5 and the second blade surface portion 6 to be formed with a helical surface twisting gently from the connecting position with the third blade surface portion 7 toward the needle point 8. Accordingly, the penetration resistance at the time of puncturing the human body can be further reduced as compared with the case where there is variation in the angular change amount of the angle θ.

Figure 4:
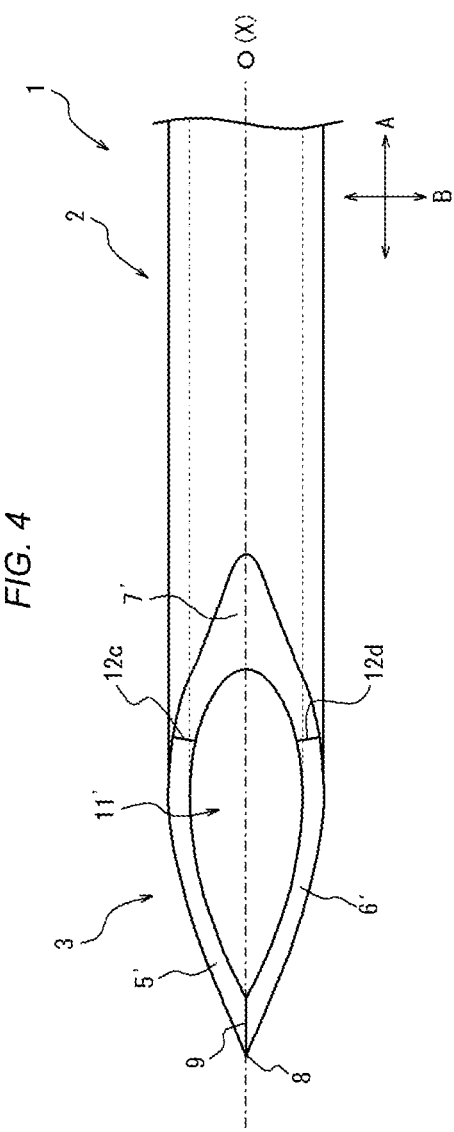
FIG. 4 is a diagram illustrating a modification of a blade surface illustrated in FIGS. 1A-1D.

While the opening 11 at one end of the hollow portion 10 in the center axis direction A is mainly sectioned by the inner edge 13 of the first blade surface portion 5 and the inner edge 14 of the second blade surface portion 6 in the present embodiment, as illustrated in FIG. 2A, the configuration is not limited to such a configuration. For example, as illustrated in FIG. 4, it is allowable to configure such that the connecting position between a first blade surface portion 5'/second blade surface portion 6' and the third blade surface portion 7' is provided in a region in which an opening 11' is located in the center axis direction A in a plan view of FIG. 4. That is, a boundary line 12c serving as a connecting position between the first blade surface portion 5' and the third blade surface portion 7' and a boundary line 12d serving as a connecting position between the second blade surface portion 6' and the third blade surface portion 7' may be provided at positions sandwiching the opening 11', so as to section the opening 11' by the edge of each of the first blade surface portion 5', the second blade surface portion 6', and the third blade surface portion 7'. Note that on the boundary lines 12c and 12d as illustrated in FIG. 4, smooth connections avoiding formation of ridgelines are also achieved at a position between the first blade surface portion 5' and the third blade surface portion 7' and the position between the second blade surface portion 6' and the third blade surface portion 7'. Moreover, while the boundary lines 12c and 12d extend along an orthogonal direction B orthogonal to the center axis direction A in the plan view of FIG. 4, the boundary lines 12c and 12d may be configured to extend in parallel with the orthogonal direction B or extend with inclination at a predetermined angle with respect to the orthogonal direction B, in a plan view of FIG. 4. Furthermore, while the third blade surface portion 7' is constituted solely with a protruding curved surface, the third blade surface portion 7' may be configured to include a partially protruding curved surface, that is, include a portion continuing from the boundary lines 12c and 12d as a plane, and include a protruding curved surface at a position extending further toward the main body portion 2 side from the end portion on the main body portion 2 side of the opening 11' in the center axis direction A, for example.

Note that while the puncture needle 1 according to the present embodiment is a hollow needle that sections the hollow portion 10, it may be a solid needle not sectioning the hollow portion 10.

Second Embodiment

Figure 5A:
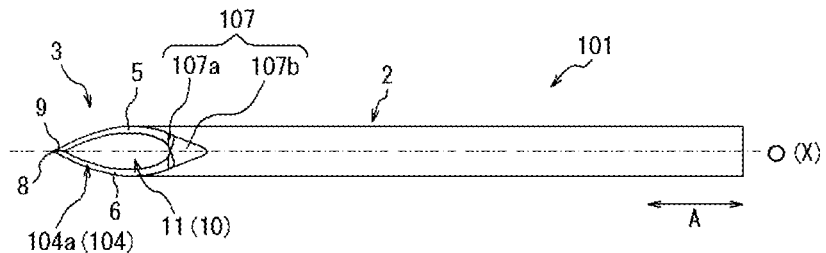
Figure 5B:
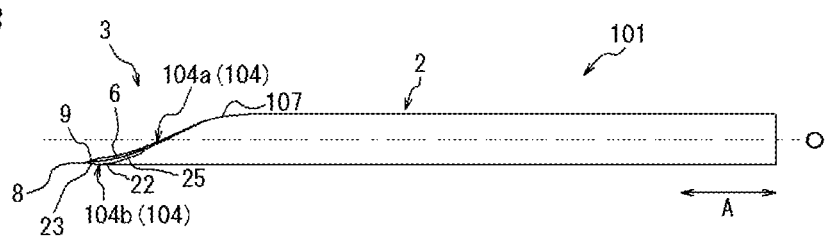
Figure 5C:
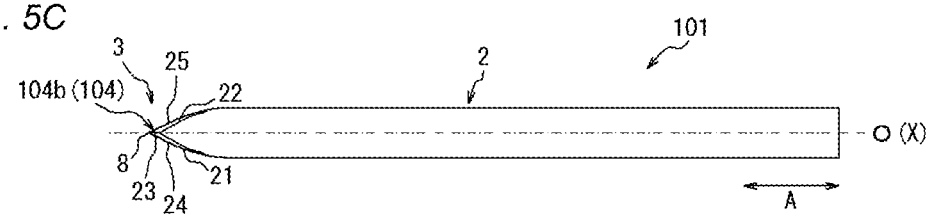
Figure 5D:
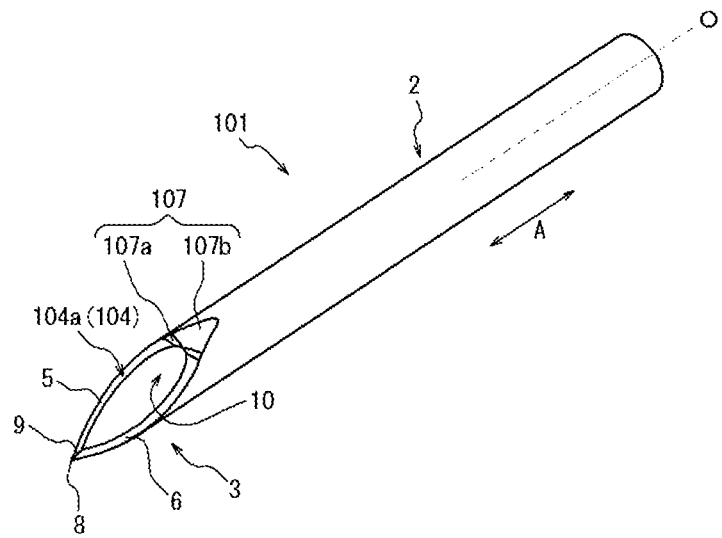

Next, a puncture needle 101 according to another embodiment of the present invention will be described. FIGS. 5A-5D are diagrams illustrating the puncture needle 101. Specifically, FIG. 5A is a plan view of a front side of the puncture needle 101, FIG. 5B is a side view of the puncture needle 101, FIG. 5C is a plan view of the back side of the puncture needle 101. FIG. 5D is a perspective view of the puncture needle 101. FIGS. 6A and 6B are enlarged views of the distal end portion 3 illustrated in FIGS. 5A and 5B, respectively. FIGS. 7A, 7B, 7C, 7D, 7E, and 7F are cross sectional views taken along lines V-V, VI-VI, VII-VII, VIII-VIII, IX-IX, and X-X, respectively, in FIGS. 6A and 6B.

While the puncture needle 101 illustrated in FIGS. 5 to 7 differs from the above-described puncture needle 1 in the configuration of the blade surface, the configurations of the other portions are common with the puncture needle 1. Accordingly, the configuration of the puncture needle 101 different from the configuration of the above-described puncture needle 1 will be mainly described, and the description of the configurations common with the puncture needle 1 will be omitted.

As illustrated in FIGS. 5A to 5D, the puncture needle 101 includes the main body portion 2 and the distal end portion 3, and the distal end portion 3 includes a blade surface 104. The blade surface 104 has a front side blade surface 104a and a back side blade surface 104b formed on the back side of the front side blade surface 104a. In other words, the puncture needle 101 according to the present embodiment includes the blade surface 104 formed with back-cut processing.

The front side blade surface 104a of the blade surface 104 includes the first blade surface portion 5, the second blade surface portion 6, and a third blade surface portion 107. Since the details of the first blade surface portion 5 and the second blade surface portion 6 are as described above, the description thereof will be omitted.

The third blade surface portion 107 according to the present embodiment is continuous with the outer circumferential surface of the main body portion 2 on the main body portion 2 side in the center axis direction A and continuous with the first blade surface portion 5 and the second blade surface portion 6 on the needle point 8 side in the center axis direction A. The third blade surface portion 107 has a protruding curved surface. Specifically, the third blade surface portion 107 according to the present embodiment is constituted with solely a protruding curved surface continuous with the first blade surface portion 5 and the second blade surface portion 6. Furthermore, the third blade surface portion 107 is constituted with a protruding curved surface in which the angle θ with respect to the center plane X in the cross section orthogonal to the center axis direction A is substantially constant regardless of the position in the center axis direction A.

More specifically, as illustrated in FIGS. 5 and 6, the third blade surface portion 107 according to the present embodiment includes a distal end side portion 107a continuous with the first blade surface portion 5 and the second blade surface portion 6 on the needle point 8 side in the center axis direction A, and includes a proximal end side portion 107b continuous with the main body portion 2 side of the distal end side portion 107a in the center axis direction A. The distal end side portion 107a and the proximal end side portion 107b are formed with protruding curved surfaces having different curvatures in a side view (refer to FIGS. 5B and 6B). Moreover, each of the distal end side portion 107a and the proximal end side portion 107b is constituted with a curved surface in which the angle θ with respect to the center plane X in the cross section orthogonal to the center axis direction A is substantially constant regardless of the position in the center axis direction A. The portion between the first blade surface portion 5/second blade surface portion 6 and the distal end side portion 107a, and the portion between the distal end side portion 107a and the proximal end side portion 107b are smoothly continuous portions so as not to form a ridgeline.

In other words, in the present embodiment, the distal end side portion 107a and the proximal end side portion 107b having different curvatures of the puncture needle 101 in a side view (refer to FIGS. 5B and 6B) are continuously arranged in the center axis direction A, so as not to from a ridgeline to be penetration resistance between the first blade surface portion 5/second blade surface portion 6 and the third blade surface portion 107. That is, the distal end side portion 107a of the third blade surface portion 107 is a connecting curved surface for smoothly connecting the first blade surface portion 5 and the second blade surface portion 6 to the proximal end side portion 107b of the third blade surface portion 107, with the curvature in a side view being greater than the curvature of the proximal end side portion 107b.

More specifically, as illustrated in FIG. 6A, the distal end side portion 107a according to the present embodiment is constituted with a first connecting curved surface 130a and a second connecting curved surface 130b. The first connecting curved surface 130a is located between the first blade surface portion 5 and the proximal end side portion 107b in the center axis direction A. The second connecting curved surface 130b is located between the second blade surface portion 6 and the proximal end side portion 107b in the center axis direction A. Note that while FIG. 6A includes a line representing a boundary line at each of the portion between the first blade surface portion 5 and the first connecting curved surface 130a of the distal end side portion 107a, the portion between the second blade surface portion 6 and the second connecting curved surface 130b of the distal end side portion 107a, the portion between the first connecting curved surface 130a and the proximal end side portion 107b, and the portion between the second connecting curved surface 130b and the proximal end side portion 107b, these lines merely represent boundaries and do not represent the ridgelines formed by the surfaces intersecting each other. As described above, the first blade surface portion 5 is smoothly connected to the proximal end side portion 107b via the first connecting curved surface 130a of the distal end side portion 107a, and the second blade surface portion 6 is smoothly connected to the proximal end side portion 107b via the second connecting curved surface 130b of the distal end side portion 107a. In FIGS. 5A and 5D, the line drawn between the first blade surface portion 5/second blade surface portion 6 and the distal end side portion 107a and the line drawn between the distal end side portion 107a and the proximal end side portion 107b simply represent the boundary lines similarly to the description above.

The back side blade surface 104b of the blade surface 104 includes a fourth blade surface portion 21 formed on the back side of the first blade surface portion 5 and includes a fifth blade surface portion 22 formed on the back side of the second blade surface portion 6. The fourth blade surface portion 21 and the fifth blade surface portion 22 intersect each other to be a ridgeline and form a blade edge 23 with the needle point 8 as one end by the ridgeline, on the needle point 8 side in the center axis direction A.

The first blade surface portion 5 and the fourth blade surface portion 21 intersect each other to be a ridgeline and form a blade edge 24 having the needle point 8 as one end by the ridgeline. More specifically, the blade edge 24 is constituted with the ridgeline formed by the outer edge of the first blade surface portion 5 and the outer edge of the fourth blade surface portion 21.

Furthermore, the second blade surface portion 6 and the fifth blade surface portion 22 intersect each other to be a ridgeline and form a blade edge 25 having the needle point 8 as one end by the ridgeline. More specifically, the blade edge 25 is constituted with the ridgeline formed by the outer edge of the second blade surface portion 6 and the outer edge of the fifth blade surface portion 22.

Hereinafter, for convenience of description, the blade edge 9 formed by the ridgeline on which the first blade surface portion 5 and the second blade surface portion 6 intersect each other will be referred to as "a first blade edge 9", the blade edge 23 formed by the ridgeline on which the fourth blade surface portion 21 and the fifth blade surface portion 22 intersect each other will be referred to as "a second blade edge 23", the blade edge 24 formed by the ridgeline on which the first blade surface portion 5 and the fourth blade surface portion 21 intersect each other will be referred to as "a third blade edge 24", and the blade edge 25 formed by the ridgeline on which the second blade surface portion 6 and the fifth blade surface portion 22 intersect each other will be referred to as "a fourth blade edge 25".

In this manner, the puncture needle 101 according to the present embodiment includes the back side blade surface 104b in addition to the front side blade surface 104a, making it possible to form the needle point 8 of the puncture needle 101 to be sharper than the case of the above-described puncture needle 1 and to further reduce the penetration resistance in the vicinity of the needle point 8.

Similarly to the first blade surface portion 5 and the second blade surface portion 6, the fourth blade surface portion 21 and the fifth blade surface portion 22 according to the present embodiment change the angle on a cross section orthogonal to the center axis direction A depending on the position on the center axis direction A. Specifically, in a case where one virtual plane including the center axis O of the main body portion 2 is established, each of the fourth blade surface portion 21 and the fifth blade surface portion 22 according to the present embodiment is constituted with a curved surface in which an angle γ with respect to the one virtual plane in a cross section orthogonal to the center axis direction A gradually increases toward the needle point 8 side in the center axis direction A. Note that it is possible to establish the virtual plane on the center plane X in the puncture needle 101 according to the present embodiment, and each of the fourth blade surface portion 21 and the fifth blade surface portion 22 according to the present embodiment is constituted with a curved surface in which an angle γ with respect to the center plane X in a cross section orthogonal to the center axis direction A gradually increases toward the needle point 8 side in the center axis direction A.

By forming each of the fourth blade surface portion 21 and the fifth blade surface portion 22 with the curved surface described above, it is possible to sharpen the portion in the vicinity of the needle point 8, and achieve a configuration unlikely to form a ridgeline (junction) having a possibility of becoming penetration resistance between the fourth blade surface portion 21/fifth blade surface portion 22 and the outer circumferential surface of the tubular member constituting the puncture needle 101.

Hereinafter, the shape of the blade surface 104 according to the present embodiment will be described in detail with reference to FIGS. 7A-7F.

Figure 7A:
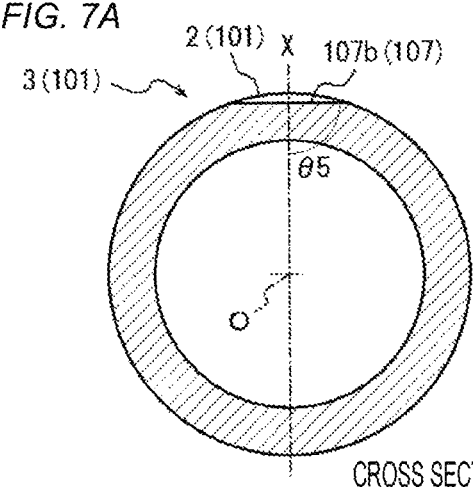
FIGS. 7A, 7B, 7C, 7D, 7E, and 7F are cross sectional views taken along lines V-V, VI-VI, VII-VII, VIII-VIII, IX-IX, and X-X, respectively, in FIGS. 6A and 6B.

FIG. 7A illustrates a cross section taken along line V-V in FIGS. 6A and 6B, that is, a cross section passing through the proximal end side portion 107b of the third blade surface portion 107 and orthogonal to the center axis direction A. As illustrated in FIG. 7A, an angle θ5 of the proximal end side portion 107b with respect to the center plane X in cross section V-V in FIGS. 6A and 6B is about 90 degrees, and the angle θ of the proximal end side portion 107b according to the present embodiment with respect to the center plane X is about 90 degrees regardless of the position in the center axis direction A, namely, any position other than on cross section V-V in FIGS. 6A and 6B. In other words, as illustrated in FIG. 7A, the proximal end side portion 107b on the third blade surface portion 107 according to the present embodiment extends linearly in a direction orthogonal to the center plane X in the cross section orthogonal to the center axis direction A.

Figure 7B:
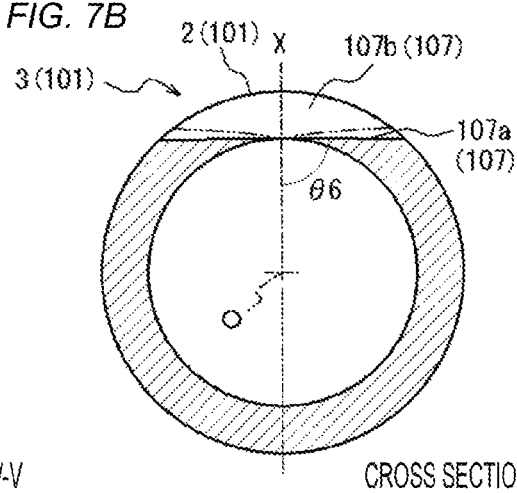

FIG. 7B illustrates a cross section taken along line VI-VI in FIGS. 6A and 6B, that is, a cross section passing through the distal end side portion 107a of the third blade surface portion 107 and orthogonal to the center axis direction A. As illustrated in FIG. 7B, an angle θ6 of the distal end side portion 107a with respect to the center plane X in cross section VI-VI in FIGS. 6A and 6B is about 90 degrees, and the angle θ of the distal end side portion 107a according to the present embodiment with respect to the center plane X is about 90 degrees regardless of the position in the center axis direction A, namely, any position other than on section VI-VI in FIGS. 6A and 6B. In other words, as illustrated in FIG. 7B, the distal end side portion 107a on the third blade surface portion 107 according to the present embodiment extends linearly in a direction orthogonal to the center plane X in the cross section orthogonal to the center axis direction A. Note that in FIG. 7B and FIGS. 7C to 7F to be referred to below, the boundary line between the distal end side portion 107a and the proximal end side portion 107b on the third blade surface portion 107 is indicated by a two-dot chain line.

Figure 7C:
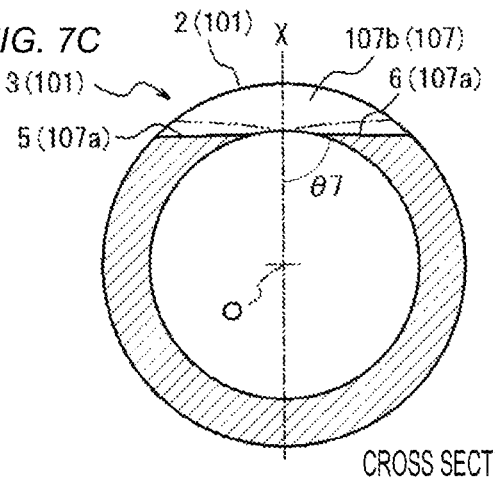

FIG. 7C is a cross section taken along line VII-VII in FIGS. 6A and 6B, that is, a cross section orthogonal to the center axis direction A at a position where the first blade surface portion 5 and the second blade surface portion 6 are connected to the distal end side portion 107a of the third blade surface portion 107 in the center axis direction A. As illustrated in FIG. 7C, each of the first blade surface portion 5 and the second blade surface portion 6 has an angle θ7 with respect to the center plane X in cross section VII-VII in FIGS. 6A and 6B is about 90 degrees, linearly extending in a direction orthogonal to the center plane X as illustrated in FIG. 7C. In other words, the first blade surface portion 5 and the second blade surface portion 6 are smoothly connected to each other without forming ridgelines with the distal end side portion 107a.

Figure 7D:
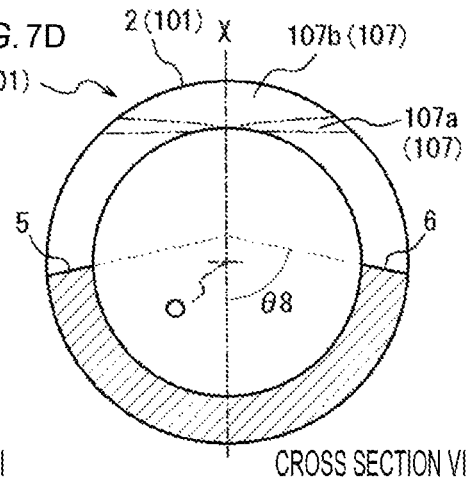

FIG. 7D is a cross sectional view taken a long line VIII-VIII in FIGS. 6A and 6B, that is, a cross section orthogonal to the center axis direction A at a position where the first blade surface portion 5 and the second blade surface portion 6 are formed in the center axis direction A and at the same time, at a position where the fourth blade surface portion 21 and the fifth blade surface portion 22 are not formed. As illustrated in FIG. 7D, an angle θ8 of each of the first blade surface portion 5 and the second blade surface portion 6 in section VIII-VIII in FIGS. 6A and 6B with respect to the center plane X is an acute angle smaller than the angle θ7. Note that in FIG. 7D and in FIGS. 7E and 7F to be referred to below, the boundary line between the first blade surface portion 5/second blade surface portion 6 and the distal end side portion 107a of the third blade surface portion 107 is indicated by a two-dot chain line.

Figure 7E:
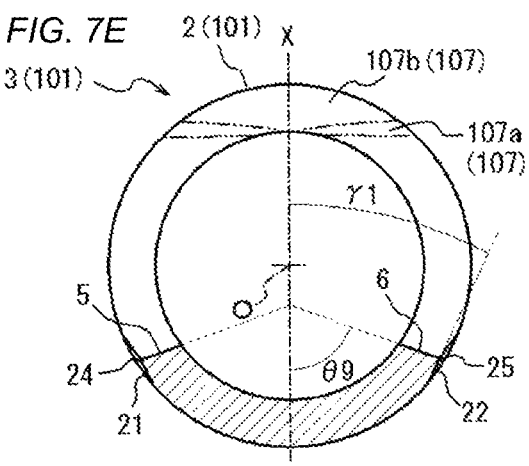

FIG. 7E is a cross sectional view taken along line IX-IX in FIGS. 6A and 6B, that is, a cross section orthogonal to the center axis direction A at a position where the first blade surface portion 5, the second blade surface portion 6, the fourth blade surface portion 21, and the fifth blade surface portion 22 are formed in the center axis direction A and at the same time, at a position where the opening 11 is provided in the center axis direction A. In other words, FIG. 7E is a cross section orthogonal to the center axis direction A at a position where the first blade edge 9 and the second blade edge 23 are not formed in the center axis direction A and at the same time, at a position where the third blade edge 24 and the fourth blade edge 25 are formed. As illustrated in FIG. 7E, an angle θ9 of each of the first blade surface portion 5 and the second blade surface portion 6 in cross section IX-IX in FIGS. 6A and 6B with respect to the center plane X is an acute angle smaller than the angle θ7 and smaller than the angle θ8.

Moreover, as illustrated in FIG. 7E, the fourth blade surface portion 21 and the fifth blade surface portion 22 are formed in cross section IX-IX in FIGS. 6A and 6B, and each of the fourth blade surface portion 21 and the fifth blade surface portion 22 extends linearly at a predetermined acute angle γ1 with respect to the center plane X in a cross sectional view of FIG. 7E.

Figure 7F:
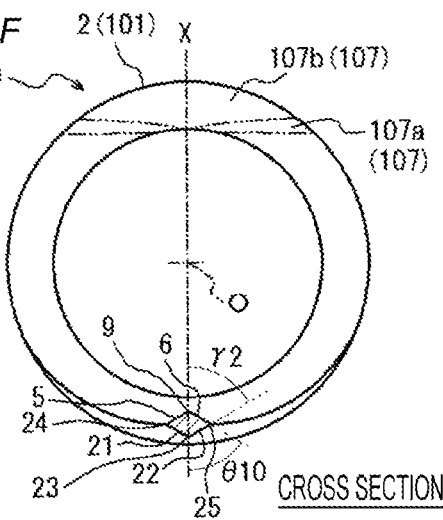

FIG. 7F illustrates a cross section taken along line X-X in FIGS. 6A and 6B, that is, a cross section orthogonal to the center axis direction A at a position where the first blade edge 9, the second blade edge 23, the third blade edge 24, and the fourth blade edge 25 are formed. As illustrated in FIG. 7F, an angle θ10 of each of the first blade surface portion 5 and the second blade surface portion 6 in cross section X-X in FIGS. 6A and 6B with respect to the center plane X is an acute angle smaller than the angle θ7, smaller than the angle θ8, and smaller than the angle θ9.

Moreover, as illustrated in FIG. 7F, an angle γ2 of each of the fourth blade surface portion 21 and the fifth blade surface portion 22 with respect to the center plane X in cross section X-X in FIGS. 6A and 6B is an acute angle greater than the angle γ1.

In this manner, the first blade surface portion 5 and the second blade surface portion 6 are straight lines in a cross sectional view orthogonal to the center axis direction A, and the angle θ of each of the first blade surface portion 5 and the second blade surface portion 6 according to the present embodiment with respect to the center plane X in the cross section orthogonal to the center axis direction A gradually decreases toward the needle point 8 side (in a closer position to the needle point 8) in the center axis direction A (refer to FIGS. 7C to 7F). Moreover, the fourth blade surface portion 21 and the fifth blade surface portion 22 are straight lines in a cross sectional view orthogonal to the center axis direction A, and the angle γ of each of the fourth blade surface portion 21 and the fifth blade surface portion 22 according to the present embodiment with respect to the center plane X in the cross section orthogonal to the center axis direction A gradually increases toward the needle point 8 side (in a closer position to the needle point 8) in the center axis direction A (refer to FIGS. 7E and 7F).

Note that while FIGS. 7C to 7F illustrate the angles θ7 to θ10 of the second blade surface portion 6 with respect to the center plane X respectively, the angles of the first blade surface portion 5 with respect to the center plane X are also the same as the angles θ7 to θ10 of the second blade surface portion 6. Note that while FIGS. 7E and 7F illustrate the angles γ1 and γ2 of the fifth blade surface portion 22 with respect to the center plane X respectively, the angles of the fourth blade surface portion 21 with respect to the center plane X are also the same as the angles γ1 and γ2 of the fifth blade surface portion 22. Furthermore, the four cross sections in FIGS. 7C to 7F are merely examples to illustrate the size relationship between the angles θ7 to θ10 and the size relationship between the angles γ1 and γ2, and the size relationship of the above-described angles θ and γ is not limited to these four cross sections.

While the puncture needle 101 according to the present embodiment is configured such that both the fourth blade surface portion 21 and the fifth blade surface portion 22 are constituted with curved surfaces in which the angle γ with respect to the center plane X in a cross section orthogonal to the center axis direction A gradually increases toward the needle point 8 side in the center axis direction A, it is also allowable to configure such that any one of the fourth blade surface portion 21 and the fifth blade surface portion 22 is constituted with such a curved surface while the other is constituted with a plane or a curved surface having another surface shape. Moreover, both the fourth blade surface portion 21 and the fifth blade surface portion 22 may be constituted with a plane or a curved surface having another surface shape. With a configuration, however, used in the present embodiment, in which both the fourth blade surface portion 21 and the fifth blade surface portion 22 are constituted with curved surfaces in which the angle γ with respect to the center plane X in a cross section orthogonal to the center axis direction A gradually increases toward the needle point 8 side in the center axis direction A, it is possible to further sharpen the portion in the vicinity of the needle point 8 and facilitate achieving the configuration that is unlikely to form a ridgeline (junction) having a possibility of becoming the penetration resistance between the fourth blade surface portion 21/fifth blade surface portion 22 and the outer circumferential surface of the tubular member constituting the puncture needle 101.

Third Embodiment

Next, a puncture needle 51 according to the embodiment of the present invention will be described. FIGS. 8 and 9 are diagrams illustrating the puncture needle 51, in which FIG. 8A is a perspective view of a portion in the vicinity of a distal end portion 53 of the puncture needle 51, FIG. 8B is a plan view of the front side in the vicinity of the distal end portion 53 of the puncture needle 51, and FIGS. 9A, 9B, 9C, 9D, 9E and 9F are cross sectional views taken along lines XI-XI, XII-XII, XIII-XIII, XIV-XIV, XV-XV, and XVI-XVI in FIG. 8B, respectively.

The puncture needle 51 includes a main body portion 52 and the distal end portion 53, and sections a hollow portion 60 communicating from the main body portion 52 to the distal end portion 53. The puncture needle 51 according to the present embodiment is different from the above-described puncture needle 1 according to the first embodiment in the shape of a blade surface 54, and other configurations are common in both. Therefore, the shape of the blade surface 54 will mainly be described here.

Figure 8A:
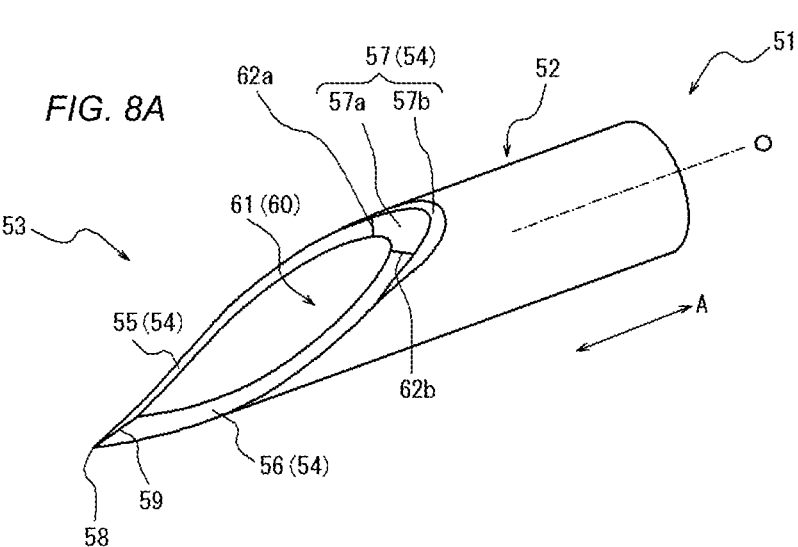
Figure 8B:
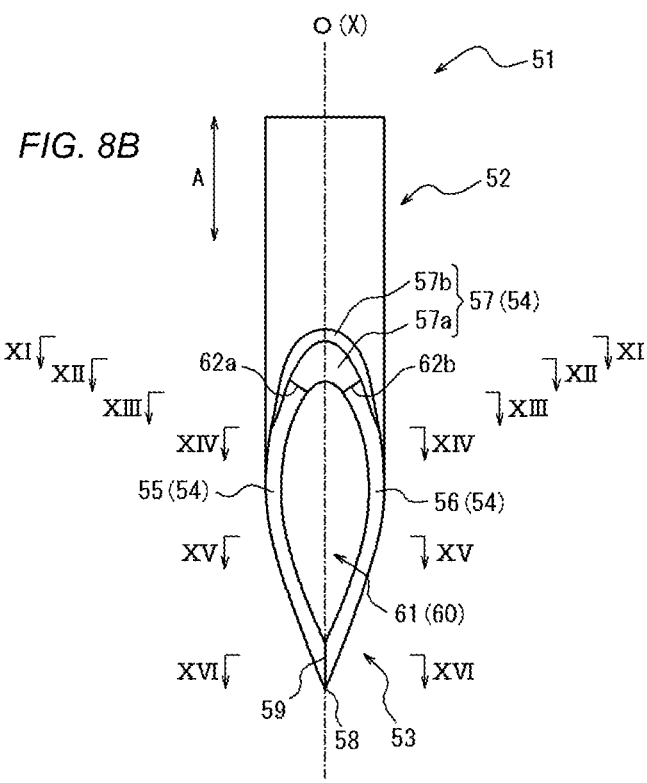

As illustrated in FIGS. 8A and 8B, the distal end portion 53 includes the blade surface 54, and the blade surface 54 includes a first blade surface portion 55 and a second blade surface portion 56 formed with a curved surfaces, and includes a third blade surface portion 57 formed with a plane and a curved surface. The first blade surface portion 55 and the second blade surface portion 56 intersect each other to be a ridgeline and form a blade edge 59 having a needle point 58 as one end by the ridgeline. Note that the "needle point" represents the distal end of the puncture needle 51 in the center axis direction A of the main body portion 52, similarly to the above-described first embodiment.

The third blade surface portion 57 is continuous with the outer circumferential surface of the main body portion 52 on the main body portion 52 side in the center axis direction A and continuous with the first blade surface portion 55 and the second blade surface portion 56 on the needle point 58 side in the center axis direction A.

More specifically, the first blade surface portion 55 and the second blade surface portion 56 are continuous with the third blade surface portion 57 on the main body portion 52 side in the center axis direction A, and intersect each other on the needle point 58 side and form a ridgeline, namely, a blade edge 59. Moreover, the first blade surface portion 55 and the second blade surface portion 56 in the present embodiment section an opening 61, that is, one end of the hollow portion 60 on the distal end portion 53 side.

Similarly to the second blade surface portion 6 according to the above-described first embodiment, the second blade surface portion 56 changes the angle on a cross section orthogonal to the center axis direction A depending on the position on the center axis direction A. Specifically, the second blade surface portion 56 is constituted with a curved surface, similar to a helical surface, for example, extending in a twisted manner from the position continuous with the third blade surface portion 57 toward the needle point 58 in the center axis direction A. Similarly to the first blade surface portion 5 in the above-described first embodiment, the first blade surface portion 55 is also constituted with a curved surface extending in a twisted manner from the position continuous with the third blade surface portion 57 toward the needle point 58 in the center axis direction A. Note that the directions of twisting of the first blade surface portion 55 and the second blade surface portion 56 toward the needle point 58 side are opposite to each other.

In other words, similarly to the case of the first blade surface portion 5 and the second blade surface portion 6 in the above-described first embodiment, in a case where one virtual plane including the center axis O of the main body portion 52 is established, each of the first blade surface portion 55 and the second blade surface portion 56 is constituted with a curved surface in which the angle θ with respect to the one virtual plane in a cross section orthogonal to the center axis direction A gradually decreases toward the needle point 58 side in the center axis direction A. In short, the puncture needle 51 according to the present embodiment is a puncture needle capable of defining such one virtual plane.

Here, the puncture needle 51 according to the present embodiment includes one plane that can be defined as the above-described "virtual plane". Specifically, the puncture needle 51 according to the present embodiment enables the above-described "virtual plane" to be established in the center plane X as a plane including the center axis O and the needle point 58, and is configured such that each of the first blade surface portion 55 and the second blade surface portion 56 is constituted with a curved surface in which the angle θ with respect to the center plane X in a cross section orthogonal to the center axis direction A gradually decreases toward the needle point 58 side in the center axis direction A. Note that the center plane X according to the present embodiment is a plane including not solely the needle point 58 but also the blade edge 59.

While the puncture needle 51 according to the present embodiment is configured such that both the first blade surface portion 55 and the second blade surface portion 56 are constituted with curved surfaces in which the angle θ with respect to the center plane X in a cross section orthogonal to the center axis direction A gradually decreases toward the needle point 58 side in the center axis direction A, it is also allowable to configure such that any one of the first blade surface portion 55 and the second blade surface portion 56 is constituted with such a curved surface while the other is constituted with a plane or a curved surface having another surface shape. Besides, both the first blade surface portion 55 and the second blade surface portion 56 may be constituted with a plane or a curved surface having another surface shape. Still, similarly to the first blade surface portion 5 and the second blade surface portion 6 according to the above-described first embodiment, it is preferable that both the first blade surface portion 55 and the second blade surface portion 56 are constituted with curved surfaces in which the angle θ with respect to the center plane X in a cross section orthogonal to the center axis direction A gradually decreases toward the needle point 58 side in the center axis direction A.

Moreover, the third blade surface portion 57 according to the present embodiment includes a plane portion 57a continuous with the first blade surface portion 55 and the second blade surface portion 56, and includes a curved surface portion 57b as a protruding curved surface continuous with the first blade surface portion 55, the second blade surface portion 56, and the plane portion 57a.

The plane portion 57a is a plane inclined at a predetermined angle with respect to the center axis direction A and has an arch-like or arcuate shape curved so as to follow the inner edge of the opening 61 on the main body portion 52 side in the plan view illustrated in FIG. 8B. Moreover, in the plan view of FIG. 8B, the outer edge on one end side of the arch-like or arcuate plane portion 57a forms a boundary line 62a with the first blade surface portion 55, and the outer edge on the other end side forms a boundary line 62b with the second blade surface portions 56. The shape of the plane portion 57a in the plan view of FIG. 8B is not limited to the arch-like or arcuate shape in the present embodiment, but may be formed into shapes such as a fan shape spreading radially from the inner edge end portion of the opening 61 on the main body portion 52 side, and a mountain shape formed with a straight line passing through the inner edge end portion of the opening 61 on the main body portion 52 side and with an arch-like curved line connecting both ends of this straight line.

In the present embodiment, the boundary lines 62a between the first blade surface portion 55 and the plane portion 57a and the boundary line 62b between the second blade surface portion 56 and the plane portion 57a of the third blade surface portion 57 are smoothly continuous with each other so as not to form a ridgeline (junction), and thus, the boundary lines 62a and 62b illustrated in FIG. 8B are not the line representing the ridgelines but the lines simply indicating the boundaries. Alternatively, it is also allowable to form the boundary lines 62a and 62b by ridgelines that would not significantly increase the penetration resistance.

The curved surface portion 57b as a protruding curved surface is located on the main body portion 52 side of the plane portion 57a in the center axis direction A and is formed continuously with the plane portion 57a. Moreover, the curved surface portion 57b is not merely located on the main body portion 52 side of the plane portion 57a but also extends in a circumferential direction of the puncture needle 51 so as to be continuous with the outer edge of the first blade surface portion 55 and the second blade surface portion 56. That is, the curved surface portion 57b is continuous with each of the first blade surface portion 55, the second blade surface portion 56, and the plane portions 57a of the third blade surface portion 57 at different positions in the circumferential direction of the puncture needle 51.

Moreover, the curved surface portion 57b is continuous with the outer circumferential surface of the main body portion 52 on the main body portion 52 side in the center axis direction A.

The curved surface portion 57b as a protruding curved surface is constituted with a curved surface in which the angle δ with respect to the center plane X in a cross section orthogonal to the center axis direction A gradually decreases toward the needle point 58 side in the center axis direction A. Details of the shape of the third blade surface portion 57 will be described below.

Hereinafter, the blade surface 54 according to the present embodiment will be described in detail. The configuration of the blade edge 59 is similar to the case of the blade edge 9 of the above-described first embodiment, the description thereof will be omitted.

[First Blade Surface Portion 55 and Second Blade Surface Portion 56 of the Distal End Portion 53]

As illustrated in FIG. 8B, each of the first blade surface portion 55 and the second blade surface portion 56 is continuous with the third blade surface portion 57 on the main body portion 52 side in the center axis direction A. More specifically, each of the first blade surface portion 55 and the second blade surface portion 56 is continuous with the plane portion 57a and the curved surface portion 57b of the third blade surface portion 57 on either side across the center plane X.

FIG. 9C is a cross section taken along line XIII-XIII in FIG. 8B, that is, a cross section orthogonal to the center axis direction A at a position where the first blade surface portion 55 and the second blade surface portion 56 are connected to the plane portion 57a of the third blade surface portion 57 in the center axis direction A. As illustrated in FIG. 9C, an angle θ13 of each of the first blade surface portion 55 and the second blade surface portion 56 in cross section XIII-XIII in FIG. 8B with respect to the center plane X is about 90 degrees. In other words, in cross section XIII-XIII in FIG. 8B, each of the first blade surface portion 55 and the second blade surface portion 56 extends linearly in a direction orthogonal to the center plane X. In FIG. 9C and FIG. 9D to FIG. 9F to be referred to below, the boundary lines 62a and 62b are indicated by two-dot chain lines.

FIG. 9D is a cross section taken along line XIV-XIV in FIG. 8B, that is, a cross section orthogonal to the center axis direction A, at a position more toward the needle point 58 side than the case of cross section XIII-XIII in FIG. 8B in the center axis direction A, in other words, a cross section orthogonal to the center axis direction A, including a point closest to the needle point 58 side on the curved surface portion 57b of the third blade surface portion 57. As illustrated in FIG. 9D, an angle θ14 of each of the first blade surface portion 55 and the second blade surface portion 56 in cross section XIV-XIV in FIG. 8B with respect to the center plane X is an acute angle smaller than the angle θ13.

FIG. 9E illustrates a cross section taken along line XV-XV in FIG. 8B, that is, the cross section orthogonal to the center axis direction A, at a point more toward the needle point 58 side than the case of cross section XIV-XIV in FIG. 8B in the center axis direction A. As illustrated in FIG. 9E, an angle θ15 of each of the first blade surface portion 55 and the second blade surface portion 56 in cross section XV-XV in FIG. 8B with respect to the center plane X is an acute angle smaller than the angle θ13 and smaller than the angle θ14.

FIG. 9F illustrates a cross section taken along line XVI-XVI in FIG. 8B, that is, a cross section orthogonal to the center axis direction A at a position where the blade edge 59 is formed in the center axis direction A. As illustrated in FIG. 9F, an angle θ16 of each of the first blade surface portion 55 and the second blade surface portion 56 in cross section XVI-XVI in FIG. 8B with respect to the center plane X is an acute angle smaller than the angle θ13 and smaller than the angle θ14, and further smaller than the angle θ15.

In this manner, the first blade surface portion 55 and the second blade surface portion 56 are straight lines in a cross sectional view orthogonal to the center axis direction A (refer to FIGS. 9C to 9F), and the angle θ of each of the first blade surface portion 55 and the second blade surface portion 56 according to the present embodiment with respect to the center plane X in the cross section orthogonal to the center axial direction A gradually decreases toward the needle point 58 side (in a closer position to the needle point 58) in the center axis direction A. Note that while FIGS. 9C to 9F illustrate the angles θ13 to θ16 of the second blade surface portion 56 with respect to the center plane X respectively, the angles of the first blade surface portion 55 with respect to the center plane X are also the same as the angles θ13 to θ16 of the second blade surface portion 56. The four cross sections in FIGS. 9C to 9F are merely examples to illustrate the size relationship between the angles θ13 to θ16, and the size relationship of the above-described angles θ is not limited to these four cross sections.

As illustrated in FIGS. 9C to 9F, while the second blade surface portion 56 according to the present embodiment is a straight line in a cross section orthogonal to the center axis direction A, the configuration is not limited to this configuration. For example, it is possible to form the second blade surface portion to have an arcuate cross section with a curved line, orthogonal to the center axis direction A, or have the cross section with a straight line and an arcuate curve continuous with this straight line. This also applies to the first blade surface portion in a similar manner. In this case, the angle θ of the first blade surface portion and the second blade surface portion indicates the angle formed by a straight line passing through an inner edge and an outer edge of each of the first blade surface portion and the second blade surface portion in the cross section orthogonal to the center axis direction A, and by one established virtual plane (center plane X in the present embodiment).

[Third Blade Surface Portion 57 of Distal End Portion 53]

As described above, the third blade surface portion 57 includes the plane portion 57a and the curved surface portion 57b as a protruding curved surface.

As described above, the plane portion 57a of the third blade surface portion 57 is a plane inclined at a predetermined angle with respect to the center axis direction A. Therefore, an angle λ of the plane portion 57a with respect to the center plane X in the cross section orthogonal to the center axis direction A is substantially constant regardless of the position in the center axis direction A. Specifically, as illustrated in FIG. 9B, an angle λ1 with respect to the center plane X of the plane portion 57a according to the present embodiment on the cross section XII-XII in FIG. 8B is about 90 degrees, and the angle λ of the plane portion 57a according to the present embodiment with respect to the center plane X is about 90 degrees regardless of the position in the center axis direction A, namely, any position other than on cross section XII-XII in FIG. 8B. In other words, as illustrated in FIG. 9B, in the cross section orthogonal to the center axis direction A, the plane portion 57a according to the present embodiment extends linearly in a direction orthogonal to the center plane X.

The curved surface portion 57b according to the present embodiment is a protruding curved surface in which the angle δ with respect to the center plane X in the cross section orthogonal to the center axis direction A changes depending on the position in the center axis direction A. FIG. 9A is a cross section taken along line XI-XI in FIG. 8B, that is, a cross section orthogonal to the center axis direction A, including solely the curved surface portion 57b of the third blade surface portion 57, on the blade surface 54. As illustrated in FIG. 9A, the curved surface portion 57b according to the present embodiment in cross section XI-XI in FIG. 8B has a protruding arcuate shape with a curvature smaller than the curvature of the main body portion 52.

As illustrated in FIG. 9B, in the cross section taken along line XII-XII in FIG. 8B, that is, in the cross section orthogonal to the center axis direction A at a position on more toward the needle point 58 side in the center axis direction A than the case of FIG. 9A, and at a position including the plane portion 57a and the curved surface portion 57b, an angle δ1 of the curved surface portion 57b with respect to the center plane X is an acute angle smaller than 90 degrees.

As illustrated in FIG. 9C, in the cross section taken along line XIII-XIII in FIG. 8B, that is, in the cross section orthogonal to the center axis direction A at a position on more toward the needle point 58 side in the center axis direction A than the case of FIG. 9B and at a position including the curved surface portion 57b, an angle δ2 of the curved surface portion 57b with respect to the center plane X is an acute angle smaller than the angle δ1.

In this manner, the angle δ of the curved surface portion 57b of the third blade surface portion 57 with respect to the center plane X in the cross section orthogonal to the center axis direction A gradually decreases toward the needle point 58 side (in a closer position to the needle point 58) in the center axis direction A, (refer to FIGS. 9B and 9C). While FIGS. 9B and 9C respectively illustrate the angles δ1 and δ2 with respect to the center plane X for the portion located on the right side of the center plane X in the curved surface portion 57b of the third blade surface portion 57, the same is applied to the angle of the portion located on the left side of the center plane X with respect to the center plane X. The two cross sections in FIGS. 9B and 9C are merely examples to illustrate the size relationship between the angles δ1 and δ2, and the size relationship of the above-described angles δ is not limited to these two cross sections.

With the blade surface 54 according to the present embodiment, it is possible to obtain the effect similar to the effects of the blade surface 4 of the above-described first embodiment. Furthermore, by constituting the curved surface portion 57b with the curved surface in which the angle δ with respect to the center plane X in a cross section orthogonal to the center axis direction A gradually decreases toward the needle point 58 side in the center axis direction A as described in the present embodiment, it is possible to form the blade surface length M (refer to FIG. 8B) of the blade surface 54 in the center axis direction A compared with the case of forming the third blade surface portion 7 in a curved surface shape in the above-described first embodiment. This makes it easier to achieve the puncture needle 51 capable of placing the entire blade surface 54 in the vessel.

As illustrated in FIG. 9B and FIG. 9C, by adopting the curved surface shape of the curved surface portion 57b of the present embodiment, a ridgeline is likely to be formed between the curved surface portion 57b and each of the first blade surface portion 55 and the second blade surface portion 56. Still, it is possible to avoid this ridgeline functioning as a junction by adopting the configuration in which the ridgeline extends in the direction along the center axis direction A as illustrated in the present embodiment.

Here, while the puncture needle 51 according to the present embodiment is a hollow needle that defines the hollow portion 61, it can be a solid needle not sectioning the hollow portion 61. FIGS. 10 and 11 illustrate a puncture needle 71 which is a solid needle as a modification of the puncture needle 51 according to the present embodiment.

The puncture needle 71 illustrated in FIGS. 10 and 11 is different from the puncture needle 51 according to the present embodiment in that the hollow portion is not sectioned, and other configurations are common in both.

Figure 10A:
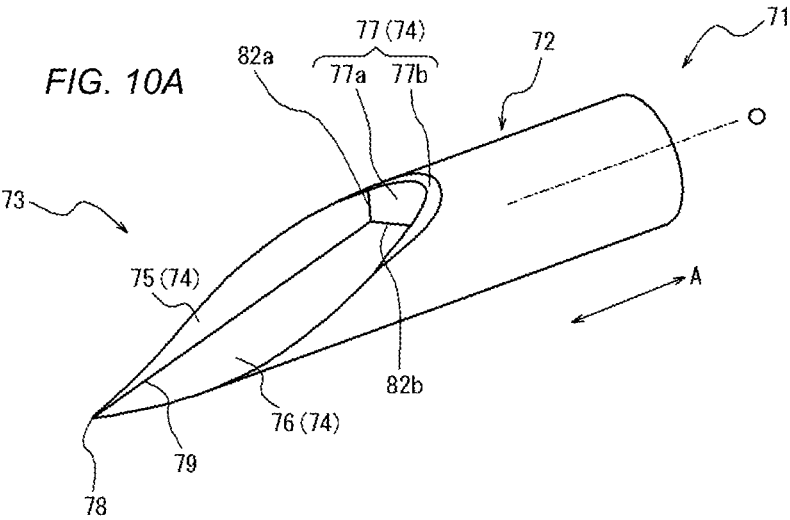
FIG. 10A is a perspective view of a puncture needle as a modification of the puncture needle illustrated in FIGS. 8A and 8B.
Figure 10B:
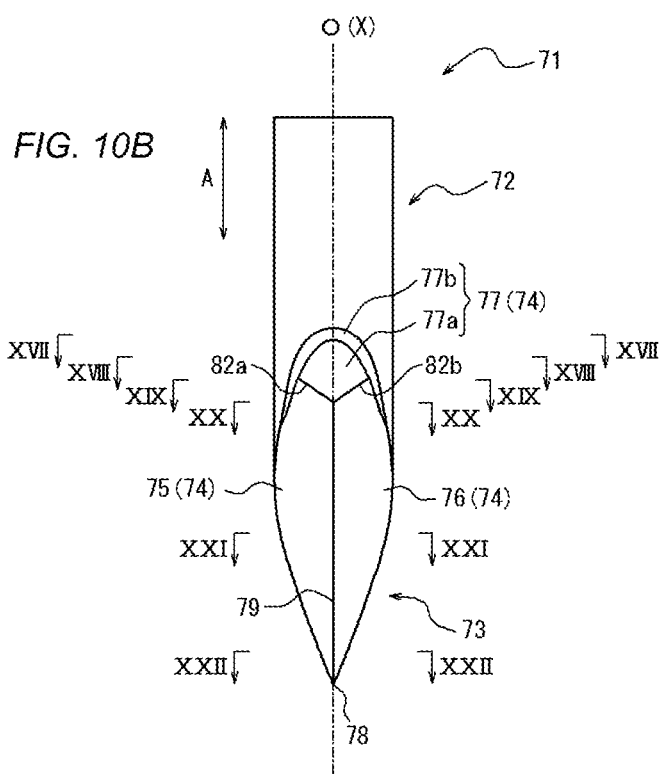
FIG. 10B is a plan view of a front side in the vicinity of the distal end portion.

FIG. 10A is a perspective view of the puncture needle 71, FIG. 10B is a plan view of the front side in the vicinity of a distal end portion 73 of the puncture needle 71, and FIGS. 11A, 11B, 11C, 11D, 11E, and 11F are cross sectional views taken along lines XVII-XVII, XVIII-XVIII, XIX-XIX, XX-XX, XXI-XXI, and XXII-XXII in FIG. 10B, respectively.

The puncture needle 71 illustrated in FIGS. 10 and 11 is a solid needle including a main body portion 72 and the distal end portion 73. The main body portion 72 has a solid rod-like shape. The distal end portion 73 includes a blade surface 74, and the blade surface 74 includes a first blade surface portion 75 and a second blade surface portion 76, formed with curved surfaces, and includes a third blade surface portion 77 having a plane portion 77a and a curved surface portion 77b as a protruding curved surface. The first blade surface portion 75 and the second blade surface portion 76 intersect each other to be a ridgeline and form a blade edge 79 with a needle point 78 as one end by the ridgeline on the center plane X.

Since the puncture needle 71 does not section the hollow portion, the first blade surface portion 75 and the second blade surface portion 76 are greater in width than the first blade surface portion 55 and the second blade surface portion 56 according to the present embodiment, respectively. The blade edge 79 formed by intersecting the first blade surface portion 75 and the second blade surface portion 76 on the center plane X is longer than the blade edge 59 according to the present embodiment. Moreover, the plane portion 77a of the third blade surface portion 77 is continuous with the first blade surface portion 75 and the second blade surface portion 76 at positions of the boundary lines 82a and 82b, respectively, and has a fan shape in a plan view illustrated in FIG. 10B. The shape of the blade surface 74 of the puncture needle 71 is the same as the shape of the blade surface 54 of the puncture needle 51 according to the present embodiment except for these points.

Figure 11A:
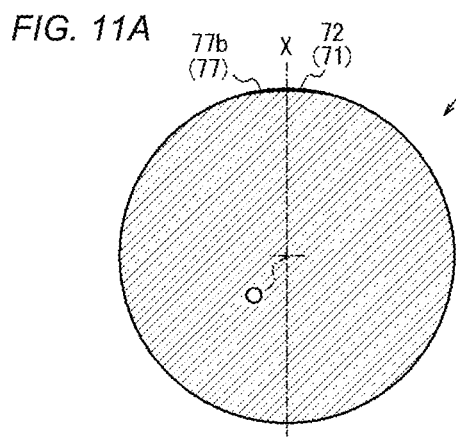
FIGS. 11A, 11B, 11C, 11D, 11E and 11F are cross sectional views taken along lines XVII-XVII, XVIII-XVIII, XIX-XIX, XX-XX, XXI-XXI, and XXII-XXII, respectively, in FIG. 10B.
Figure 11B:
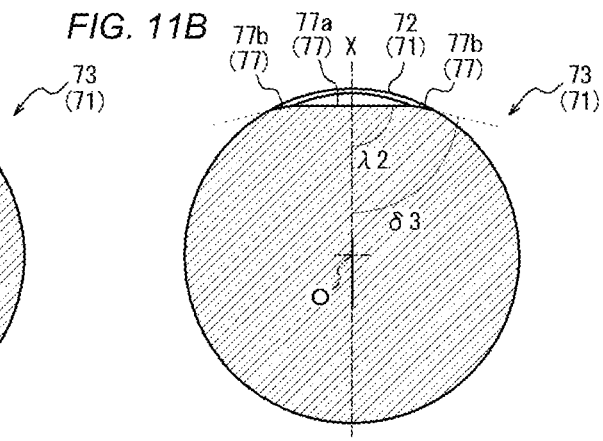
Figure 11C:
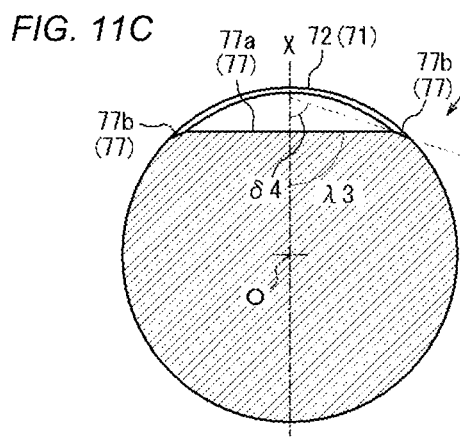
Figure 11D:
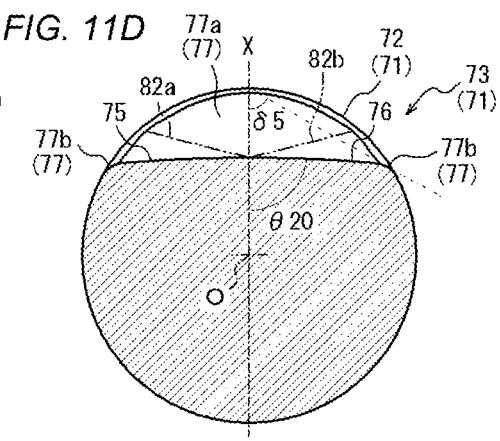
Figure 11E:
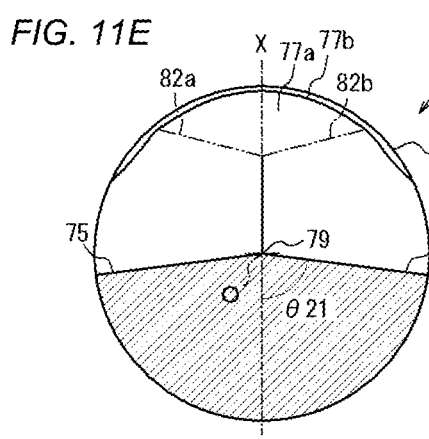
Figure 11F:
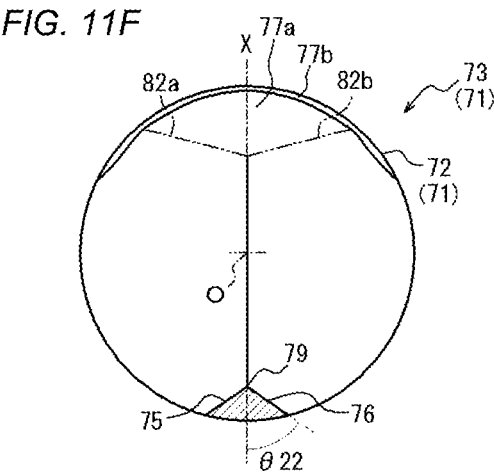

Moreover, as illustrated in FIGS. 11D to 11F, the first blade surface portion 75 and the second blade surface portion 76 are straight lines in a cross sectional view orthogonal to the center axis direction A, and the angle θ of the first blade surface portion 75 and the second blade surface portion 76 with respect to the center plane X in the cross section orthogonal to the center axis direction A gradually decreases toward the needle point 58 side (in a closer position to the needle point 58) in the center axis direction A (refer to θ20 to θ22 in FIGS. 11D to 11F). In FIG. 11 D to FIG. 11F, the boundary line 82a between the plane portion 77a and the first blade surface portion 75 and the boundary line 82b between the plane portion 77a and the second blade surface portion 76 are indicated by two-dot chain lines.

Furthermore, as illustrated in FIGS. 11B and 11C, the angle λ of the plane portion 77a with respect to the center plane X in the cross section orthogonal to the center axis direction A is substantially constant and is about 90 degrees (refer to λ2 and λ3 in FIGS. 11B and 11C) regardless of the position in the center axis direction A.

Still further, as illustrated in FIG. 11A, the curved surface portion 77b in cross section XVII-XVII in FIG. 10B has a protruding arcuate shape with a curvature smaller than the curvature of the main body portion 72. As illustrated in FIGS. 11B to 11D, the angle δ of the curved surface portion 77b of the third blade surface portion 77 with respect to the center plane X in the cross section orthogonal to the center axis direction A gradually decreases toward the needle point 78 side (closer to the needle point 78) in the center axis direction A, (refer to δ3 to δ5 FIGS. 11B to 11D).

Note that the puncture needle according to the present invention is achieved by various specific configurations and is not limited to the configurations described in the first to third embodiments. For example, it is also possible to apply the third blade surface portion 107 of the second embodiment to the third blade surface portion 7 of the puncture needle 1 of the first embodiment. Moreover, the puncture needle 101 of the second embodiment may be formed with a solid needle. Furthermore, the fourth blade surface portion 21 and the fifth blade surface portion 22 of the second embodiment may be provided on the back side of the puncture needle 51 of the third embodiment. It is within the technical scope of the present invention to combine the configurations described in the individual embodiments to constitute a new puncture needle as described above. Moreover, the puncture needle according to the present invention is not limited to the above-described embodiments, and can be modified within a range of the scope and spirit of the invention described in the appended claims. For example, while the main body portion of the puncture needle illustrated in the above-described first to third embodiments has a sectional outline having a substantially circular shape in an arbitrary transverse section, the configuration is not limited to this configuration as long as the main body portion has a hollow rod-like or a solid rod-like shape. For example, the main body portion may have a cross sectional outline having a substantially elliptical shape in an arbitrary transverse section, and the main body portion may have a cross sectional outline having any of a substantially circular shape and a substantially elliptical shape in an arbitrary transverse section. Furthermore, the main body portion may have a portion partially including the cross sectional outline formed into a substantially circular shape or a substantially elliptical shape. Still further, the shape other than the circular shape may be any shape as long as it has a flat cross sectional outline in which the major axis and the minor axis are defined, and is not limited to the elliptical shape described above and it is possible to apply, for example, a rounded rectangle obtained by combining a semicircle to either of short sides of a rectangular.

Figure 15A:
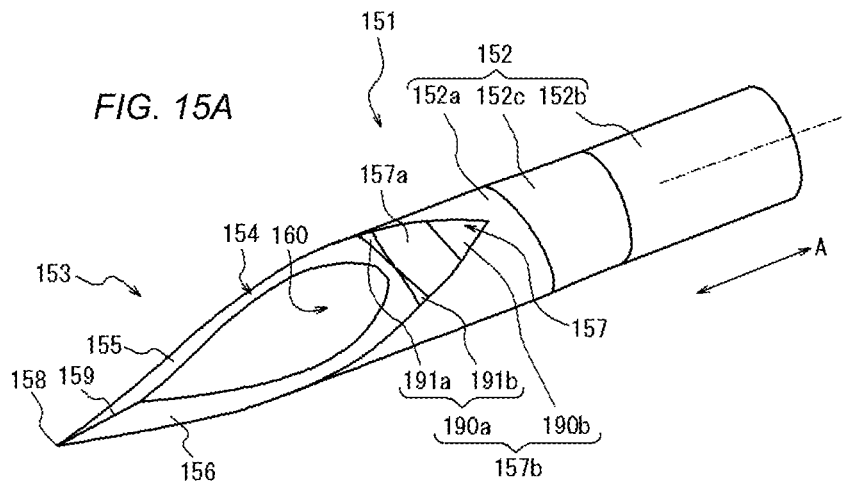
Figure 15B:
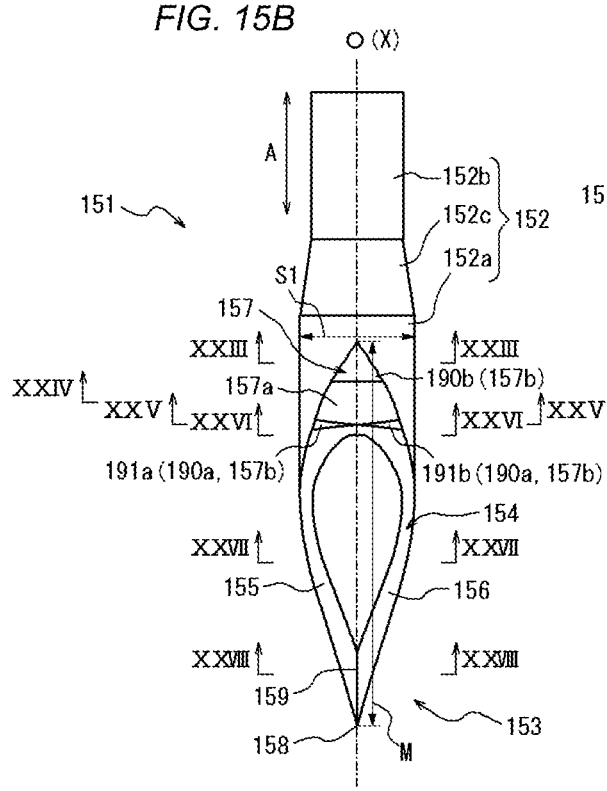
Figure 15C:
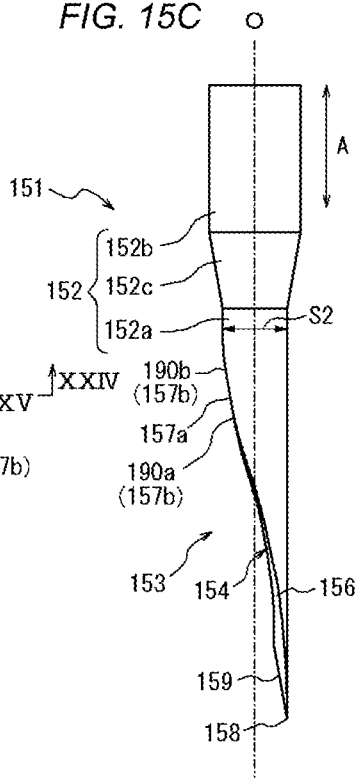

FIGS. 15 and 16 are diagrams each illustrating a puncture needle 151 including a main body portion 152 having an arbitrary transverse cross sectional outline of a substantially circular shape or a substantially elliptical shape, in which FIG. 15A is a perspective view of the vicinity of a distal end portion 153 of the puncture needle 151, FIG. 15B is a plan view of the front side of the vicinity of the distal end portion 153 of the puncture needle 151, FIG. 15C is a side view of the vicinity of the distal end portion 153 of the puncture needle 151, and FIGS. 16A, 16B, 16C, 16D, 16E, and 16F are cross sectional views taken along lines XXIII-XXIII, XXIV-XXIV, XXV-XXV, XXVI-XXVI, XXVII-XXVII, and XXVIII-XXVIII in FIG. 15B, respectively.

The puncture needle 151 illustrated in FIGS. 15 and 16 includes the main body portion 152 and the distal end portion 153, and sections a hollow portion 160 communicating from the main body portion 152 to the distal end portion 153.

The main body portion 152 is a hollow rod-like body, namely, a tubular pipe body continuous with the distal end portion 153. More specifically, the main body portion 152 includes a main body distal end portion 152a, a main body barrel portion 152b, and a linkage 152c. The main body distal end portion 152a has a substantially elliptical cross sectional outline continuous with the distal end portion 153. The main body barrel portion 152b is located on the proximal end side of the main body distal end portion 152a and has a substantially circular cross sectional outline. The linkage 152c located between the main body distal end portion 152a and the main body barrel portion 152b and connects the main body distal end portion 152a and the main body barrel portion 152b. Similarly to the above-described embodiments, the "cross sectional outline" represents a transverse cross section orthogonal to the center axis O of the main body portion 152.

The main body distal end portion 152a has a substantially elliptical cross sectional outline with a major axis having a width S1 in the plan view of FIG. 15B and a minor axis having a width S2 in a side view in FIG. 15C. As illustrated in FIGS. 15B and 15C, the width S1 as the major axis of the main body distal end portion 152a is greater than the outer diameter of the main body barrel portion 152b, and the width S2 as the minor axis of the main body distal end portion 152a is smaller than the outer diameter of the main body barrel portion 152b. Moreover, the center axis of the main body distal end portion 152a substantially matches the center axis of the main body barrel portion 152b, and the center axis O of the main body portion 152 is substantially a straight line. Accordingly, the linkage 152c has a tapered shape gradually increasing toward the distal end portion 153 side in the center axis direction A, in plan views of the front side and the back side (refer to FIG. 15B) while gradually decreasing toward the distal end portion 153 side in the center axis direction A in a side view (refer to FIG. 15C). Note that the center plane X including the center axis O and the needle point 158 is a plane including the minor axis in a cross section orthogonal to the center axis direction A of the main body distal end portion 152a.

As illustrated in FIGS. 15A to 15C, the distal end portion 153 is continuous with the main body distal end portion 152a having cross sectional outline of substantially elliptical. The distal end portion 153 includes a blade surface 154, and the blade surface 154 includes a first blade surface portion 155, a second blade surface portion 156, and a third blade surface portion 157. The first blade surface portion 155 and the second blade surface portion 156 are located across the center plane X including the minor axis. The first blade surface portion 155 and the second blade surface portion 156 are formed of curved surfaces, and intersect each other to be a ridgeline and form a blade edge 159 with the needle point 158 as one end by the ridgeline. Since the curved surface shapes of the first blade surface portion 155 and the second blade surface portion 156 are similar to the shapes of the first blade surface portion and the second blade surface portion illustrated in the first to third embodiments described above, the description thereof will be omitted.

The third blade surface portion 157 is continuous with the outer circumferential surface of the main body distal end portion 152a on the main body portion 152 side in the center axis direction A and continuous with the first blade surface portion 155 and the second blade surface portion 156 on the needle point 158 side in the center axis direction A. The third blade surface portion 157 has a protruding curved surface. More specifically, the third blade surface portion 157 includes a plane portion 157a and a curved surface portion 157b as a protruding curved surface.

The curved surface portion 157b includes a distal end side portion 190a and a proximal end side portion 190b. The distal end side portion 190a is continuous with the needle point 158 side of the plane portion 157a in the center axis direction A. The proximal end side portion 190*b* is continuous with the main body portion 152 side of the plane portion 157*a* in the center axis direction A. Both the distal end side portion 190*a* and the proximal end side portion 190*b* are portions with protruding curved surfaces. In other words, the plane portion 157*a* is located between the distal end side portion 190*a* and the proximal end side portion 190*b* in the center axis direction A.

More specifically, the distal end side portion 190*a* and the proximal end side portion 190*b* are constituted with protruding curved surfaces having different curvatures in a side view (refer to FIG. 15 C). Moreover, each of the distal end side portion 190*a* and the proximal end side portion 190*b* is constituted with a curved surface having the substantially constant angle θ with respect to the center plane X in a cross section orthogonal to the center axis direction A, regardless of the position in the center axis direction A. A portion between the first blade surface portion 155/second blade surface portion 156 and the distal end side portion 190*a*, a portion between the distal end side portion 190*a* and the plane portion 157*a*, and a portion between the plane portion 157*a* and the proximal end side portion 190*b* are smoothly continuous with each other so as not to form a ridgeline.

The distal end side portion 190*a* of the curved surface portion 157*b* is constituted with a first connecting curved surface 191*a* and a second connecting curved surface 191*b*. The first connecting curved surface 191*a* is located between the first blade surface portion 155 and the plane portion 157*a* in the center axis direction A. The second connecting curved surface 191*b* is located between the second blade surface portion 156 and the plane portion 157*a* in the center axis direction A. Note that FIGS. 15A and 15B include a line representing a boundary line at each of the portion between the first blade surface portion 155 and the first connecting curved surface 191*a* of the distal end side portion 190*a*, the portion between the second blade surface portion 156 and the second connecting curved surface 191*b* of the distal end side portion 190*a*, the portion between the first connecting curved surface 191*a* and the plane portion 157*a*, and the portion between the second connecting curved surface 191*b* and the plane portion 157*a*, these lines merely represent boundary lines and do not represent the ridgelines formed by the surfaces intersecting each other. The first blade surface portion 155 is smoothly connected to the plane portion 157*a* via the first connecting curved surface 191*a* of the distal end side portion 190*a*, and the second blade surface portion 156 is smoothly connected to the plane portion 157*a* via the second connecting curved surface 191*b* of the distal end side portion 190*a*.

Note that while the first and second connecting curved surfaces 191*a* and 191*b* are protruding curved surfaces in which the angle θ with respect to the center plane X in the cross section orthogonal to the center axis direction A is substantially constant regardless of the position in the center axis direction A, it is sufficient that the first blade surface portion 155 and the second blade surface portion 156 are protruding curved surfaces smoothly continuous with the plane portion 157*a*, and the surfaces are not limited to the protruding curved surface in which the angle θ is substantially constant regardless of the position in the center axis direction A.

Moreover, in FIGS. 15A and 15B, the line drawn between the plane portion 157*a* and the proximal end side portion 190*b* of the curved surface portion 157*b* also simply represents a boundary line similarly to the described above.

Figure 16A:
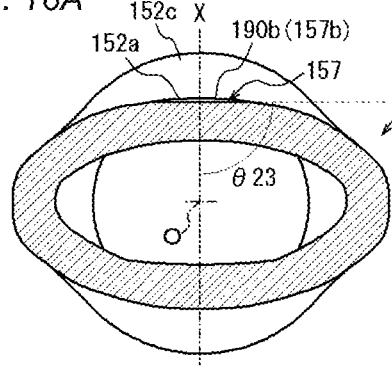
FIGS. 16A, 16B, 16C, 16D, 16E, and 16F are cross sectional views taken along lines XXIII-XXIII, XXIV-XXIV, XXV-XXV, XXVI-XXVI, XXVII-XXVII, and XXVIII-XXVIII, respectively, in FIG. 15B.

FIG. 16A illustrates a cross section taken along line XXIII-XXIII in FIG. 15B, that is, a cross section passing through the proximal end side portion 190*b* on the curved surface portion 157*b* of the third blade surface portion 157 and orthogonal to the center axis direction A. As illustrated in FIG. 16A, an angle θ23 of the proximal end side portion 190*b* with respect to the center plane X on cross section XXIII-XXIII in FIG. 15B is about 90 degrees, and the angle θ of the proximal end side portion 190*b* with respect to the center plane X is about 90 degrees regardless of the position in the center axis direction A, namely, any position other than on cross section XXIII-XXIII in FIG. 15B. In other words, as illustrated in FIG. 16A, the proximal end side portion 190*b* extends linearly in a direction orthogonal to the center plane X in the cross section orthogonal to the center axis direction A.

Figure 16B:
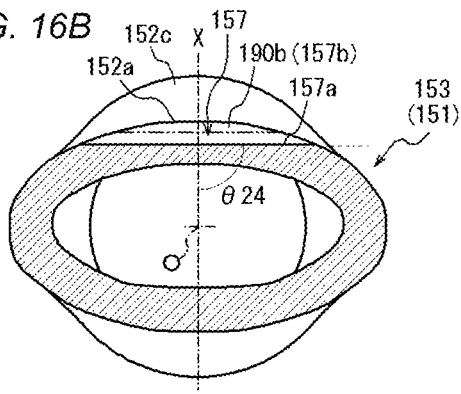

FIG. 16B illustrates a cross section taken along line XXIV-XXIV in FIG. 15B, that is, a section passing through the plane portion 157*a* of the third blade surface portion 157 and orthogonal to the center axis direction A. As illustrated in FIG. 16B, an angle θ24 of the plane portion 157*a* with respect to the center plane X on cross section XXIV-XXIV in FIG. 15B is about 90 degrees, and the angle θ of the plane portion 157*a* with respect to the center plane X is about 90 degrees regardless of the position in the center axis direction A, namely, any position other than on cross section XXIV-XXIV in FIG. 15B. In other words, as illustrated in FIG. 16B, the plane portion 157*a* of the third blade surface portion 157 extends linearly in a direction orthogonal to the center plane X in the cross section orthogonal to the center axis direction A. Note that in FIG. 16B and FIGS. 16C to 16F to be referred to below, the boundary line between the plane portion 157*a* and the proximal end side portion 190*b* is indicated by a two-dot chain line.

Figure 16C:
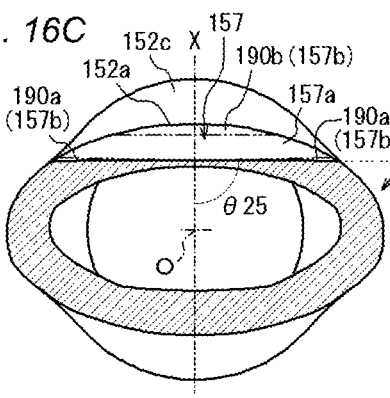

FIG. 16C illustrates a cross section taken along line XXV-XXV in FIG. 15B, that is, a cross section passing through the distal end side portion 190*a* on the curved surface portion 157*b* of the third blade surface portion 157 and orthogonal to the center axis direction A. As illustrated in FIG. 16C, an angle θ25 of the distal end side portion 190*a* with respect to the center plane X in cross section XXV-XXV in FIG. 15B is about 90 degrees, and the angle θ of the distal end side portion 190*a* with respect to the center plane X is about 90 degrees regardless of the portion in the center axis direction A, namely, any position other than on cross section XXV-XXV in FIG. 15B. In other words, as illustrated in FIG. 16C, the distal end side portion 190*a* on the curved surface portion 157*b* of the third blade surface portion 157 extends linearly in a direction orthogonal to the center plane X in the cross section orthogonal to the center axis direction A. Note that in FIG. 16C and FIGS. 16D to 16F to be referred to below, the boundary line between the distal end side portion 190*a* and the plane portion 157*a* is indicated by a two-dot chain line.

Figure 16D:
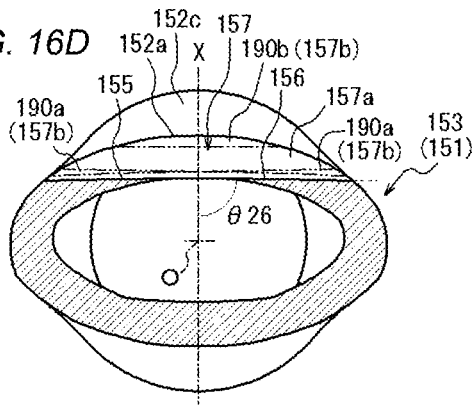
Figure 16E:
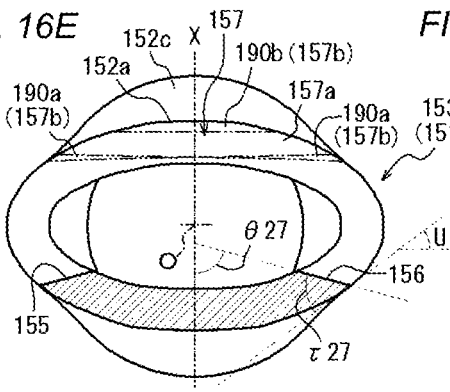
Figure 16F:
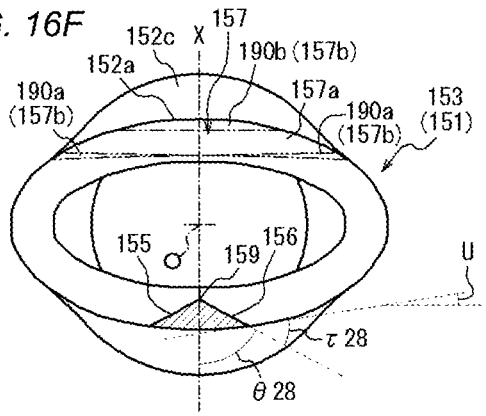

FIGS. 16D to 16F illustrate cross sections taken along lines XXVI-XXVI to XXVIII-XXVIII in FIG. 15B, respectively, that is, the cross sections passing through the first blade surface portion 155 and the second blade surface portion 156 and orthogonal to the center axis direction A. Moreover, as illustrated in FIGS. 16D to 16F, the first blade surface portion 155 and the second blade surface portion 156 are straight lines in a cross sectional view orthogonal to the center axis direction A, and the angle θ of each of the first blade surface portion 155 and the second blade surface portion 156 with respect to the center plane X in the cross section orthogonal to the center axis direction A gradually decreases toward the needle point 158 side (in a closer position to the needle point 158) in the center axis direction A (refer to θ26 to θ28 in FIGS. 16D to 16F). Note that in FIGS. 16D to 16F, the boundary line between the first blade surface portion 155/second blade surface portion 156 and the distal end side portion 190a on the curved surface portion 157b of the third blade surface portion 157 is indicated by a two-dot chain line. The θ26 illustrated in FIG. 16D is about 90 degrees, and the first blade surface portion 155 and the second blade surface portion 156 are smoothly continuous with the above-described distal end side portion 190a at the position of this boundary line.

The puncture needle 151 illustrated in FIGS. 15 and 16 differs from the puncture needle according to the first to third embodiments in the outline of the cross section orthogonal to the center axis direction A of the main body portion 152 and the distal end portion 153. Specifically, the maximum thickness of the distal end portion 153 in a side view of the puncture needle 151 (refer to FIG. 15C) is thinner than a maximum thickness of the distal end portion of the puncture needle according to the first to third embodiments in a side view (refer to FIG. 1B, or the like). In the puncture needle 151 illustrated in FIGS. 15 and 16, a minor axis of the main body distal end portion 152a in a cross section orthogonal to the center axis direction A is included in the center plane X. This configuration makes it easier to achieve the puncture needle 151 having a shorter blade surface length M, as compared with the puncture needle described in the first to third embodiments described above.

Figure 17:
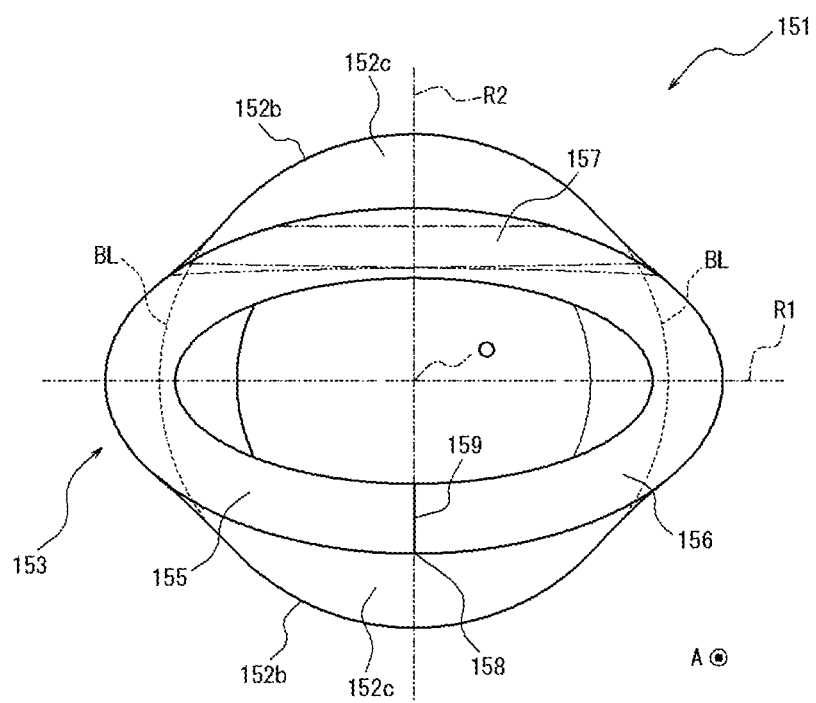
FIG. 17 is a diagram of the puncture needle illustrated in FIGS. 15A-15C as viewed from the needle point side.

FIG. 17 is a diagram of the puncture needle 151 illustrated in FIGS. 15A-15C as viewed from the needle point 158 side. In FIG. 17, "R1" indicated by a one-dot chain line indicates the major axis and "R2" indicates the minor axis. As illustrated in FIG. 17, when viewed in the center axis direction A, the needle point 158 is located inside the outer circumference of the main body barrel portion 152b (for convenience of description, a portion of the outer circumference invisible at a viewpoint of FIG. 17 is represented by broken line BL).

That is, the puncture needle 151 includes the distal end portion 153 having a flat cross sectional outline including the needle point, the main body distal end portion 152a having a flat cross sectional outline continuous with the distal end portion 153 and defined by the major axis R1 and the minor axis R2, and the main body barrel portion 152b located on more proximal end side from the main body distal end portion 152a and having a substantially circular cross sectional outline. The distal end portion 153 includes the blade surface 154. The blade surface 154 Includes the first blade surface portion 155 and the second blade surface portion 156 intersect each other to be a ridgeline to form the blade edge 159 with the needle point 158 as one end. The needle point 158 is located inside the outer circumference of the main body barrel portion 152b when viewed in the center axis direction A.

By arranging the position of the needle point 158 as viewed in the center axis direction A at this position, it is possible to form the inclination angle of the first blade surface portion 155 and the second blade surface portion 156 with respect to the center axis direction A to be smaller than the inclination angle of the first blade surface portion and the second blade surface portion with respect to the center axis direction A in the above-described comparative configuration in which the position of the needle point viewed in the center axis direction A is located on the outer circumference or outside the outer circumference of the main body barrel portion 152b, while the length of each of the first blade surface portion 155 and the second blade surface portion 156 in the center axial direction A can be formed to be equal to the length of the first blade surface portion and the second blade surface portion in the center axis direction A in the above-described comparative configuration. This configuration makes it easier to achieve the first blade surface portion 155 and the second blade surface portion 156 capable of reducing the pressing force applied from the body tissue toward the back side during the puncture. That is, this configuration makes it easier to achieve the puncture needle 151 capable of enhancing rectilinearity.

Moreover, as described above, by arranging the position of the needle point 158 when viewed in the center axis direction A to be the position inside the outer circumference of the main body barrel portion 152b, it is possible to further decrease the blade tip angle α while each of the first blade surface portion 155 and the second blade surface portion 156 in the center axis direction A is formed to have a same length as compared with the configuration in which the position of the needle point when viewed in the center axis direction A is on the outer circumference of the main body barrel portion 152b or outside the outer circumference of the main body barrel portion 152b. This configuration makes it easier to achieve the puncture needle 151 having a thin blade tip and capable of alleviating the penetration resistance at the blade tip.

Moreover, while the needle point 158 is formed at one end in a minor axis direction (direction parallel to the minor axis R2 in FIG. 17) when viewed in the center axis direction A (refer to FIG. 17), the position is not limited to the position of the needle point 158 illustrated in FIG. 17 as long as it is located inside the outer circumference of the main body barrel portion 152b when viewed in the center axis direction A (refer to FIG. 17). Still, as illustrated in FIGS. 15 to 17, it is preferable that the needle point 158 is formed at a position of one end in the minor axis direction or the vicinity of the position of one end in the minor axis direction (hereinafter, the position of one end side in the minor axis direction and the position in the vicinity thereof will be referred to as "position on one end side in the minor axis direction"). With this arrangement, it is possible to form the first blade surface portion 155 and the second blade surface portion 156 at a position with a large radius of curvature in the distal end portion 153 having a flat cross sectional outline as the elliptical shape illustrated in FIG. 17, when viewed in the center axis direction A. This makes it possible to increase the ratio of the length of the cutting edge having an intersecting angle τ (refer to "τ27" in FIG. 16E and "τ28" in FIG. 16F) of a predetermined angle (e.g., 60 degrees) or less to the length of the outer edge of each of the first blade surface portion 155 and the second blade surface portion 156.

More specifically, by forming the first blade surface portion 155 and the second blade surface portion 156 at positions having a large radius of curvature, a tangential inclination angle U (refer to FIGS. 16E and 16F) of the tangent line at the position of the outer edge of the outer circumferential surface of the distal end portion 153 (tangent line at the outer edge position of each of the first blade surface portion 155 and the second blade surface portion 156) in the cross section orthogonal to the center axis direction A with respect to the major axis direction (direction parallel to the major axis R1 in FIG. 17) is less likely to change depending on the position in the center axis direction A. That is, it is possible to reduce the rate of change in the tangential inclination angle U depending on the position in the center axis direction A. This decreases the rate of change in the intersecting angle τ (refer to "τ 27" in FIG. 16E) and "τ28" in FIG. 16F) in the center axis direction A, making it possible to increase the ratio of the length of the cutting edge having an intersecting angle τ of a predetermined angle (for example, 60 degrees) or less to the length of the outer edge of each of the first blade surface portion 155 and the second blade surface portion 156.

The outer edges of the first blade surface portion 155 and the second blade surface portion 156 are portions formed by the ridgeline on which each of the first blade surface portion 155 and the second blade surface portion 156 intersects the outer circumferential surface on the back side of the distal end portion 153. The term "cutting edge" as used herein refers to a portion ranging from the needle point 158 to a predetermined length on the outer edge of the first blade surface portion 155 and the second blade surface portion 156 where the intersecting angle τ is a predetermined angle (for example, 60 degrees) or less. Moreover, the intersecting angle τ represents an angle formed by the first blade surface portion 155 and a tangent line on the outer circumferential surface at the position of the outer edge of the first blade surface portion 155 in the cross section orthogonal to the center axis direction A, and represents an angle formed by the second blade surface portion 156 and a tangent line on the outer circumferential surface at the position of the outer edge of the second blade surface portion 156 in the cross section orthogonal to the center axis direction A (refer to "τ27" in FIG. 16E and "τ28" in FIG. 16F). This cutting edge, together with the blade edge 159, incises the skin at the time of puncture. Therefore, by increasing the ratio of the cutting edge at the outer edge of each of the first blade surface portion 155 and the second blade surface portion 156, it is possible to reduce the pain sensed by the patient caused by the outer edge of each of the first blade surface portion 155 and the second blade surface portion 156 passing on the patient at the time of puncture.

It is preferable that the outer edge of at least one blade surface portion of the first blade surface portion 155 and the second blade surface portion 156 extends to the outside of the outer circumference of the main body barrel portion 152b when the distal end portion 153 is viewed in the center axis direction A (refer to FIG. 17). In the example illustrated in FIG. 17, the outer edges of both the first blade surface portion 155 and the second blade surface portion 156 extend to the outside of the outer circumference of the main body barrel portion 152b. As described above, the distal end portion 153 of the puncture needle 151 has a flat cross sectional outline, and the needle point 158 is formed at a position on one end side in the minor axis direction (direction parallel to the minor axis R2 in FIG. 17). Therefore, as described above, it is easy to provide a long cutting edge at which the intersecting angle τ is a predetermined angle (for example, 60 degrees) or less on the outer edge of each of the first blade surface portion 155 and the second blade surface portion 156. In addition, as illustrated in FIG. 17, by adopting the configuration in which the outer edge of each of the first blade surface portion 155 and the second blade surface portion 156 extends to the outside of the outer circumference of the main body barrel portion 152b when the distal end portion 153 is viewed in the center axis direction A, it is possible to easily achieve a cutting edge long in the major axis direction (direction parallel to the major axis R1 in FIG. 17) extending from the needle point 158 to the outside of the outer circumference of the main body barrel portion 152b when the distal end portion 153 is viewed in the center axis direction A. Achievement of such a long cutting edge can alleviate the pain sensed by the patient caused by the outer edge of each of the first blade surface portion 155 and the second blade surface portion 156 passing on the patient at the time of puncture.

Note that in the cross section illustrated in FIG. 16E, the outer edge of each of the first blade surface portion 155 and the second blade surface portion 156 forms a cutting edge having the intersecting angle τ27 of a predetermined angle (for example, 60 degrees) or less. That is, the outer edge of each of the first blade surface portion 155 and the second blade surface portion 156 forms a cutting edge long in the major axis direction (direction parallel to the major axis R1 in FIG. 17) extending from the needle point 158 to the outside of the outer circumference of the main body barrel portion 152b when the distal end portion 153 is viewed in the center axis direction A.

Furthermore, as in the example illustrated in FIG. 17, it is preferable that the outer edge of at least one of the first blade surface portion 155 and the second blade surface portion 156 extends from the needle point 158 to reach the position at which the width of the distal end portion 153 is maximized in the major axis direction when the distal end portion 153 is viewed in the center axis direction A. In addition, as in the example illustrated in FIG. 17, it is preferable that the outer edges of both the first blade surface portion 155 and the second blade surface portion 156 extend from the needle point 158 to reach the position at which the width of the distal end portion 153 is maximized in the major axis direction when the distal end portion 153 is viewed in the center axis direction A. With such a configuration, the cutting edge can be formed over the entire width of the distal end portion 153 in the major axis direction. By forming a cutting edge having the intersecting angle τ of a predetermined angle (for example, 60 degrees) or less over the entire width of the distal end portion 153 in the major axis direction, it is possible to alleviate the pain sensed by the patient caused by the distal end portion 153 passing on the patient at the time of puncture.

Fourth Embodiment

Figure 12:
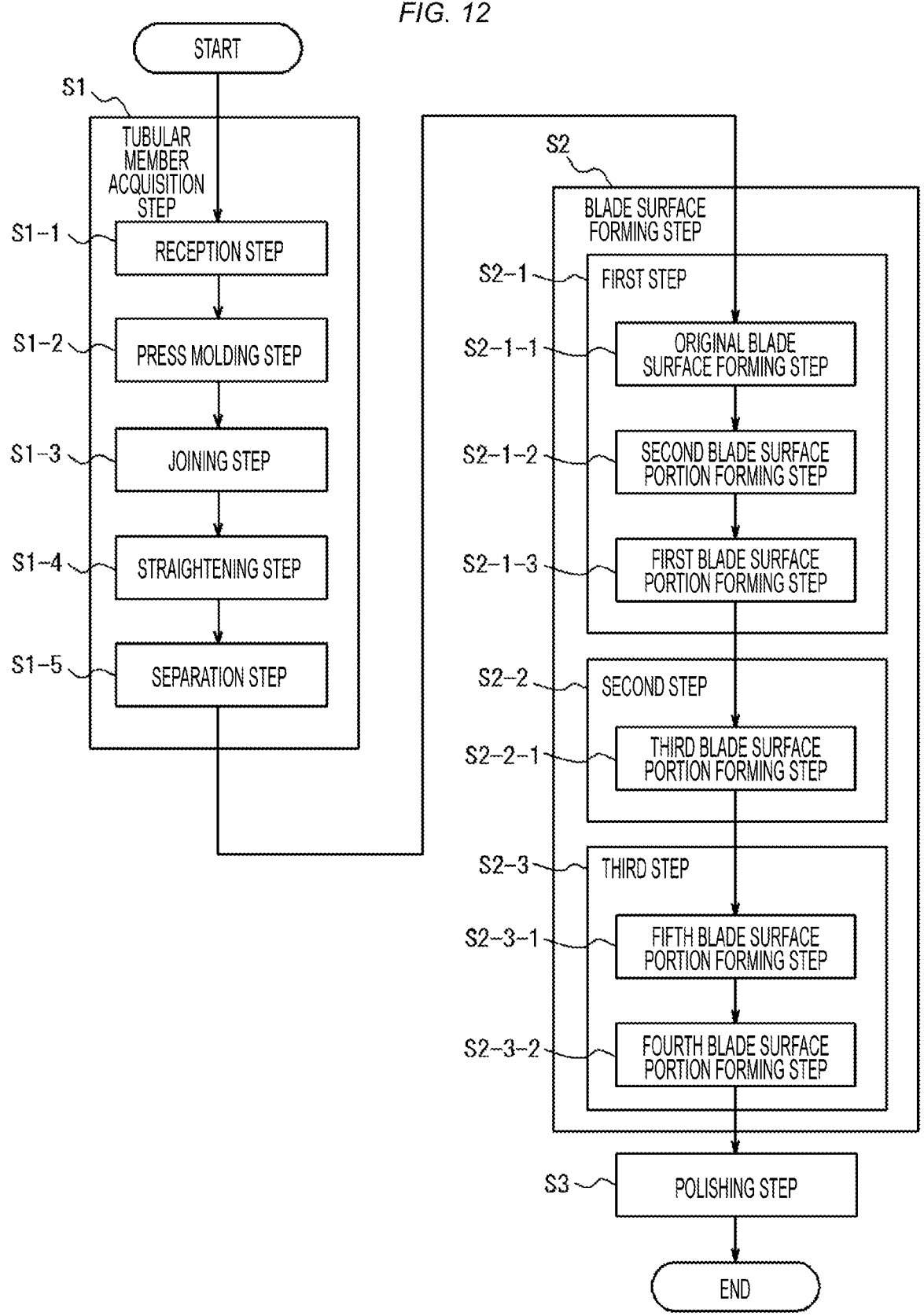
FIG. 12 is a flowchart illustrating a method for manufacturing a puncture needle according to an embodiment of the present invention.

Finally, a method for manufacturing the puncture needle 101 according to an embodiment of the present invention will be described. FIG. 12 is a flowchart illustrating a method for manufacturing the puncture needle 101 according to the present embodiment. As illustrated in FIG. 12, a method for manufacturing the puncture needle 101 includes a tubular member acquisition step S1 of obtaining a tubular member as a hollow rod-like member among the rod-like member, being a state before edge formation of the puncture needle 101, and a blade surface forming step S2 of forming the puncture needle 101 by forming the blade surface 104 (refer to FIGS. 6A and 6B, or the like) on one end portion of the tubular member by bringing at least the one end portion of the tubular member into sliding contact with a grinding surface of a rotating grindstone. The method for manufacturing the puncture needle 101 according to the present embodiment further includes a polishing step S3 of polishing the formed puncture needle 101 using various types of polishing treatment such as electrolytic polishing treatment after the blade surface forming step S2.

The tubular member acquisition step S1 can be performed by various known methods and includes: for example, a reception step S1-1 of receiving a band-shaped metallic plate material into a press molding machine; a press molding step S1-2 of obtaining a plurality of pipe bodies partially connected to the plate material successively press molded by the press molding machine; a joining step S1-3 of joining the joints of the pipe bodies with welding or an adhesive; a straightening step S1-4 of straightening the shape of the pipe body such that the center axis of the pipe body is substantially a straight line, and a separation step S1-5 of obtaining the tubular member in a state before edge formation of the puncture needle 101 by separating the pipe body from the plate material.

Figure 13A:
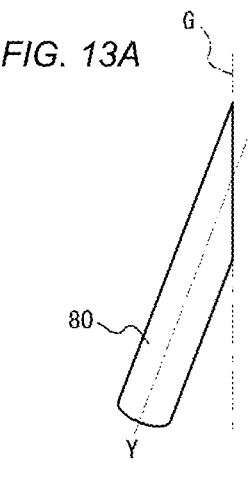
FIGS. 13A, 13B, 13C, 13D, 13E, and 13F are general views illustrating an outline of individual steps of a method for manufacturing the puncture needle illustrated in FIG. 12.
Figure 13B:
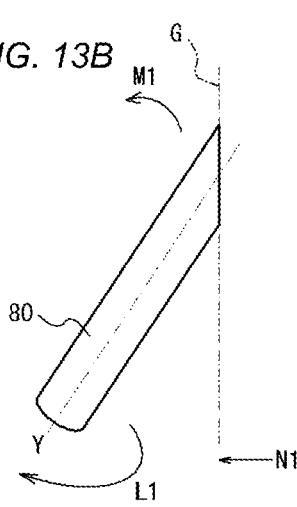
Figure 13C:
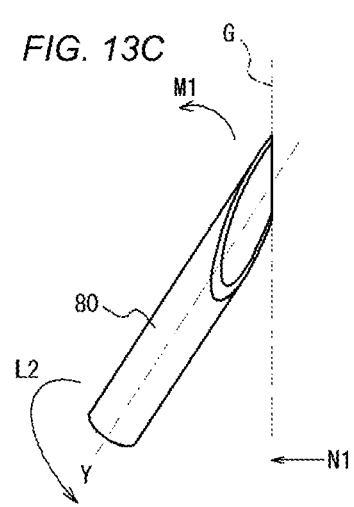
Figure 13D:
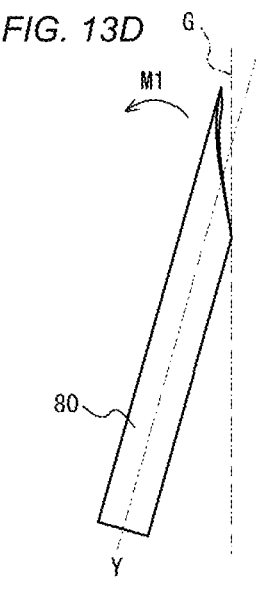
Figure 13E:
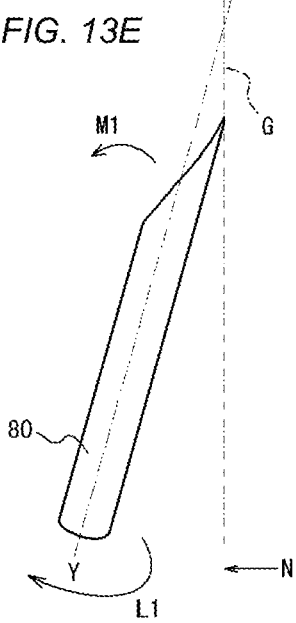
Figure 13F:
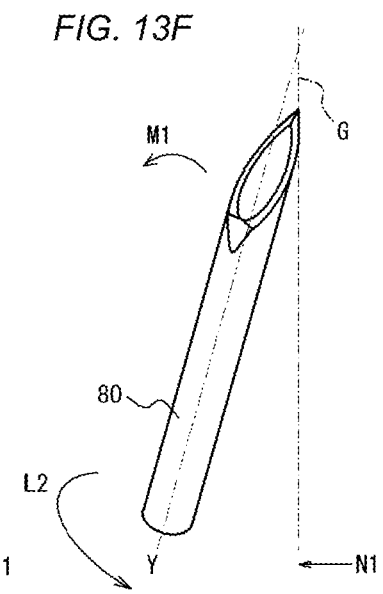

The blade surface forming step S2 includes a first step S2-1 of forming the first blade surface portion 5 and the second blade surface portion 6 (refer to FIGS. 5A-5D, or the like), a second step S2-2 of forming the third blade surface portion 107 (refer to FIGS. 5A-5D, or the like), and a third step S2-3 of forming the fourth blade surface portion 21 and the fifth blade surface portion 22 (refer to FIGS. 5A-5D, or the like). FIGS. 13A-13F are general views illustrating an outline of a method for forming the first, second, third, fourth and fifth blade surface portions 5, 6, 107, 21 and 22 in the blade surface forming step S2, in which FIG. 13A illustrates a method for forming an original blade surface in the first step S2-1, FIG. 13B illustrates a method for forming the second blade surface portion 6 in the first step S2-1, FIG. 13C illustrates a method for forming the first blade surface portion 5 in the first step S2-1, FIG. 13D illustrates a method for forming the third blade surface portion 107 in the second step S2-2, FIG. 13E illustrates a method for forming the fifth blade surface portion 22 in the third step S2-3, and FIG. 13F illustrates a method for forming the fourth blade surface portion 21 in the third step S2-3.

As illustrated in FIGS. 12 and 13, the first step S2-1 of the blade surface forming step S2 includes an original blade surface forming step S2-1-1 of forming an original blade surface before formation of the blade surface 104 of the puncture needle 101 at an end portion of the tubular member 80 formed in the above-described tubular member acquisition step S1, and includes a second blade surface portion forming step S2-1-2 of forming the second blade surface portion 6, and a first blade surface portion forming step S2-1-3 of forming the first blade surface portion 5.

The original blade surface forming step S2-1-1 forms a planar slope as an original blade surface inclined with respect to a center axis Y of the tubular member 80 by performing grinding processing using a grindstone, at an end portion of the tubular member 80. In the original blade surface forming step S2-1-1 of the present embodiment forms the original blade surface by bringing the end portion of the tubular member 80 into sliding contact with the grinding surface of the grindstone without causing the tubular member 80 to pivot and without varying the tilt angle of the center axis Y of the tubular member 80 with respect to the grinding surface of the grindstone. Alternatively, this original blade surface may be formed in the above-described press molding step S1-2 in the tubular member acquisition step S1. Moreover, the original blade surface can be formed by wire cutting, or the like, instead of the grinding processing with a grindstone. In FIGS. 13A to 13F, the grinding surface of the rotating grindstone is represented by a two-dot chain line "G".

The second blade surface portion forming step S2-1-2 and the first blade surface portion forming step S2-1-3 form the second blade surface portion 6 and the first blade surface portion 5 by grinding the original surface blade formed by the original blade surface forming step S2-1-1 located at one end portion of the tubular member 80 by bringing the original surface blade into sliding contact with the grinding surface G of the grindstone while moving the grindstone rotating in a high speed (plunge oscillation grinding).

Specifically, the second blade surface portion forming step S2-1-2 and the first blade surface portion forming step S2-1-3 form the second blade surface portion 6 and the first blade surface portion 5 (refer to FIGS. 5 and 6, or the like) as blade surface portions each being constituted with a curved surface (refer to FIGS. 13B and 13C) by bringing the original blade surface of one end portion of the tubular member 80 having a substantially circular cross sectional outline of the transverse cross section into sliding contact with the grinding surface G of the grindstone while varying the tilt angle of the center axis Y of the tubular member 80 with respect to the grinding surface G of the grindstone while causing the tubular member 80 to pivot about the center axis Y of the tubular member 80. Note that the second blade surface portion forming step S2-1-2 and the first blade surface portion forming step S2-1-3 move the grindstone to be closer to the tubular member 80 so as to maintain the sliding contact state between the grinding surface G of the grindstone and the tubular member 80 even with pivoting and variation in the inclination angle of the tubular member 80 (refer to the arrow "N1" in FIGS. 13B and 13C).

More specifically, the second blade surface portion forming step S2-1-2 can be executed by bringing the original blade surface at one end portion of the tubular member 80 into sliding contact with the grinding surface G of the grindstone while varying the tilt angle of the center axis Y of the tubular member 80 with respect to the grinding surface G of the grindstone in one tilt direction (refer to the arrow "M1" in FIG. 13B) while causing the tubular member 80 to pivot in one direction (refer to the arrow "L1" in FIG. 13B) about the center axis Y of the tubular member 80. The second blade surface portion forming step S2-1-2 forms the second blade surface portion 6. While in the second blade surface portion forming step S2-1-2, the pivoting speed and the tilting speed of the tubular member 80 can be fixed or varied in accordance with the grinding position, it is preferable to fix the speeds so as not to form a ridgeline (junction) having a possibility of becoming the penetration resistance.

Moreover, after the second blade surface portion forming step S2-1-2, the tubular member 80 is re-set to the position and posture suitable for starting the first blade surface portion forming step S2-1-3, and after completion of the re-setting, the first blade surface portion forming step S2-1-3 can be started.

The first blade surface portion forming step S2-1-3 can be executed by bringing the position of one end portion of the tubular member 80 and opposing the first blade surface portion 5 across the opening 11 (refer to FIGS. 5A-5D, or the like) into sliding contact with the grinding surface G of the grindstone while varying the tilt angle of the center axis Y of the tubular member 80 with respect to the grinding surface G of the grindstone in the same direction of the one tilt direction at the second blade surface portion forming step S2-1-2 (refer to the arrow "M1" in FIG. 13C) while causing the tubular member 80 to pivot in the direction opposite to the one direction at the second blade surface portion forming step S2-1-2 (refer to the arrow "L2" in FIG. 13C) about the center axis Y of the tubular member 80. The first blade surface portion forming step S2-1-3 forms the first blade surface portion 5 and the first blade edge 9 (refer to FIGS. 5A-5D, or the like). Similarly to the above-described second blade surface portion forming step S2-1-2, while the pivoting speed and the tilting speed of the tubular member 80 can be fixed or varied in accordance with the grinding position, in the first blade surface portion forming step S2-1-3, it is preferable to fix the speeds so as not to form a ridgeline (junction) having a possibility of becoming the penetration resistance.

In the present embodiment, the first blade surface portion forming step S2-1-3 is performed after the second blade surface portion forming step S2-1-2. Alternatively, the first blade surface portion forming step may be performed before the second blade surface portion forming step.

The second step S2-2 of the blade surface forming step S2 according to the present embodiment forms the third blade surface portion 107 (refer to FIGS. 5 and 6, or the like) as blade surface portion having a curved surface (blade surface portion constituted solely with a protruding curved surface in the present embodiment) by bringing one end portion of the tubular member 80 into sliding contact with the grinding surface of the grindstone while varying the tilt angle of the center axis Y of the tubular member 80 with respect to the grinding surface G of the grindstone without causing the tubular member 80 to pivot about the center axis Y of the tubular member 80. That is, the second step S2-2 includes the third blade surface portion forming step S2-2-1.

The second step S2-2 is executed after completion of the first blade surface portion forming step S2-1-3 of the first step S2-1. Specifically, as illustrated in FIG. 13D, the second step S2-2 can be executed by bringing the portion on the proximal end side (opposite side of the distal end side on which the blade edge 9 is formed) of the first blade surface portion 5 and the second blade surface portion 6 among one end portion of the tubular member 80 into sliding contact with the grinding surface G of the grindstone while varying the tilt angle of the center axis Y of the tubular member 80 with respect to the grinding surface G of the grindstone in the same direction of the one tilt direction at the second blade surface portion forming step S2-1-2 and the first blade surface portion forming step S2-1-3 (refer to the arrow "M1" in FIG. 13D) without causing the tubular member 80 to pivot about the center axis Y of the tubular member 80.

As described above, the third blade surface portion 107 of the puncture needle 101 includes the distal end side portion 107a and the proximal end side portion 107b having different curvatures (refer to FIGS. 5A-5D and 6A and 6B, or the like) in a side view (refer to FIG. 6B). Accordingly, in the second step S2-1, the tilting speed for varying the tubular member 80 in one tilt direction (refer to the arrow "M1" in FIG. 13D) is varied between at formation of the distal end side portion 107a and at formation of the proximal end side portion 107b. This leads to formation of the distal end side portion 107a and the proximal end side portion 107b.

The third step S2-3 of the blade surface forming step S2 according to the present embodiment forms the fourth blade surface portion 21 and the fifth blade surface portion 22 as blade surface portions constituted with curved surfaces by bringing the back side of each of the first blade surface portion 5 and the second blade surface portion 6 among one end portion of the tubular member 80 into sliding contact with a grinding surface G of the grindstone while varying the tilt angle of the center axis Y of the tubular member 80 with respect to the grinding surface G of the grindstone while causing the tubular member 80 to pivot about the center axis Y of the tubular member 80.

Specifically, the third step S2-3 according to the present embodiment includes a fifth blade surface portion forming step S2-3-1 of forming the fifth blade surface portion 22 and a fifth blade surface portion forming step S2-3-2 of forming the fourth blade surface portion 21 (refer to FIGS. 12, 13E and 13F).

As illustrated in FIG. 13E, the fifth blade surface portion forming step S2-3-1 can be executed by bringing the back side of the second blade surface portion 6 among one end portion of the tubular member 80 into sliding contact with the grinding surface G of the grindstone while varying the tilt angle of the center axis Y of the tubular member 80 with respect to the grinding surface G of the grindstone in one tilt direction (same as the tilt direction at the second blade surface portion forming step S2-1-2 in the present embodiment; refer to the arrow "M1" in FIG. 13E) while causing the tubular member 80 to pivot in one direction (same as the pivoting direction at the second blade surface portion forming step S2-1-2 in the present embodiment; refer to the arrow "L1" in FIG. 13E) about the center axis Y of the tubular member 80. The fifth blade surface portion forming step S2-3-1 forms the fifth blade surface portion 22 and the fourth blade edge 25. While in the fifth blade surface portion forming step S2-3-1, the pivoting speed and the tilting speed of the tubular member 80 can be fixed or varied in accordance with the grinding position, it is preferable to fix the speeds so as not to form a ridgeline (junction) having a possibility of becoming the penetration resistance.

After the fifth blade surface portion forming step S2-3-1, the tubular member 80 is re-set to the position and posture suitable for starting the fourth blade surface portion forming step S2-3-2, and after completion of the re-setting, the fourth blade surface portion forming step S2-3-2 can be started.

The fourth blade surface portion forming step S2-3-2 can be executed by bringing the back side of the first blade surface portion 5 among one end portion of the tubular member 80 into sliding contact with the grinding surface G of the grindstone while varying the tilt angle of the center axis Y of the tubular member 80 with respect to the grinding surface G of the grindstone in the same direction of the one tilt direction at the fifth blade surface portion forming step S2-3-1 (refer to the arrow "M1" in FIG. 13F) while causing the tubular member 80 to pivot in the direction opposite to the one direction at the fifth blade surface portion forming step S2-3-1 (same as the pivoting direction at the first blade surface portion forming step S2-1-3 in the present embodiment; refer to the arrow "L2" in FIG. 13F) about the center axis Y of the tubular member 80. The fourth blade surface portion forming step S2-3-2 forms the fourth blade surface portion 21, the second blade edge 23, and the third blade edge 24. Similarly to the fifth blade surface portion forming step S2-3-1, while the pivoting speed and the tilting speed of the tubular member 80 can be fixed or varied in accordance with the grinding position in the fourth blade surface portion forming step S2-3-2, it is preferable to fix the speeds so as not to form a ridgeline (junction) having a possibility of becoming the penetration resistance.

In the present embodiment, the fourth blade surface portion forming step S2-3-2 is performed after the fifth blade surface portion forming step S2-3-1. Alternatively, the fourth blade surface portion forming step may be performed before the fifth blade surface portion forming step.

Moreover, the fifth blade surface portion forming step S2-3-1 and the fourth blade surface portion forming step S2-3-2 according to the present embodiment move the grindstone to be closer to the tubular member 80 so as to maintain the sliding state between the grinding surface G of the grindstone and the tubular member 80 even with pivoting and variation in the inclination angle of the tubular member 80 (refer to the arrow "N1" in FIGS. 13E and 13F).

In this manner, the blade surface forming step S2 in the method for manufacturing the puncture needle 101 according to the present embodiment can form the first blade surface portion 5, the second blade surface portion 6, the fourth blade surface portion 21, and the fifth blade surface portion 22 by bringing the end portion of the tubular member 80 into sliding contact with the grinding surface G of the grindstone while rotating the grindstone, moving the grindstone, causing the tubular member 80 to pivot, and varying the tilt angle of the tubular member 80 at the same time. Moreover, the blade surface forming step S2 in the method for manufacturing the puncture needle 101 according to the present embodiment can form the third blade surface portion 107 by bringing the end portion of the tubular member 80 into sliding contact with the grinding surface G of the grindstone while rotating the grindstone, moving the grindstone, and varying the tilt angle of the tubular member 80 without causing the tubular member 80 to pivot.

While the method for manufacturing the puncture needle 101 according to the second embodiment is described in the present embodiment, it is also possible to form the first blade surface portion 55 and the second blade surface portion 56 of the puncture needle 51 according to the third embodiment (refer to FIGS. 8A and 8B, or the like.) by a method similar to the method for forming the first blade surface portion 5 and the second blade surface portion 6 according to the second embodiment. Furthermore, the plane portion 57a of the third blade surface portion 57 (refer to FIGS. 8A and 8B, or the like) of the puncture needle 51 according to the third embodiment can be formed by the method similar to the above-described method for forming the original blade surface, and the curved surface portion 57b (refer to FIGS. 8A and 8B, or the like) can be formed by bringing the portion into sliding contact with the grinding surface G of the grindstone while rotating the grindstone, moving the grindstone, causing the tubular member to pivot, and varying the tilt angle of the tubular member at the same time, similarly to the above-described method for forming the first blade surface portion 5 and the second blade surface portion 6. Moreover, the puncture needle 151 illustrated in FIGS. 15 and 16 can be configured such that one end portion on which the blade surface 154 is formed has a substantially elliptical cross sectional outline by applying press-work onto the one end portion of the cylindrical tubular member in the tubular member acquisition step S1 or immediately before the original blade surface forming step S2-1-1. The puncture needle 71 illustrated in FIGS. 10 and 11 can be configured such that a solid rod-like member is formed by a known solid rod-like member acquisition step of forming a solid rod-like member instead of the above-described tubular member acquisition step S1, and that the blade surface 74 is formed on one end portion of the solid rod-like member with a method similar to the above-described blade surface forming step S2.

REFERENCE NUMERAL LIST 1, 51, 71, 101, 151 Puncture needle
2, 52, 72, 152 Main body portion
3, 53, 73, 153 Distal end portion
4, 54, 74, 104, 154 Blade surface
5, 5', 55, 75, 155 First blade surface portion
6, 6', 56, 76, 156 Second blade surface portion
7, 7', 57, 77, 107, 157 Third blade surface portion
8, 58, 78, 158 Needle point
9, 59, 79, 159 Blade edge (first blade edge)
10, 60, 160 Hollow portion
11, 11', 61 Opening
12a to 12d, 62a, 62b, 82a, 82b Boundary line
13 Inner edge of first blade surface portion
14 Inner edge of second blade surface portion
21 Fourth blade surface portion
22 Fifth blade surface portion
23 Blade edge (second blade edge)
24 Blade edge (third blade edge)
25 Blade edge (fourth blade edge)
57a, 77a, 157a Plane portion
57b, 77b, 157b Curved surface (protruding curved surface)
80 Tubular member (rod-like member)
104a Front side blade surface
104b Back side blade surface
107a, 190a Distal end side portion
107b, 190b Proximal end side portion
130a, 191a First connecting curved surface
130b, 191b Second connecting curved surface
152a Main body distal end portion
152b Main body barrel portion
152c Linkage
A Center axis direction
B Direction orthogonal to center axis direction (orthogonal direction)
G Grinding surface of grindstone
K Point on third blade surface portion in center plane
L Straight line connecting needle point and the point on third blade surface portion in center plane
M Blade surface length
O Center axis
P Body surface
Q Incision on body surface
Q1 Edge portion of incision
R1 Major axis
R2 Minor axis
S1, S2 Width of main body distal end portion
U Tangential inclination angle
X Center plane
Y Center axis of tubular member
W Width of third blade surface portion
α Blade tip angle
θ Angles of first to third blade surface portions with respect to center plane in cross section orthogonal to center axis direction
γ Angles of fourth and fifth blade surface portions with respect to center plane in cross section orthogonal to center axis direction
δ Angle of curved surface portion of third blade surface portion with respect to center plane in cross section orthogonal to center axis direction
λ Angle of plane portion of third blade surface portion with respect to center plane in cross section orthogonal to center axis direction
τ Intersecting angle

What is claimed is:

1. A medical puncture needle comprising: a distal end portion including a needle point; and a rod-like main body portion continuous with the distal end portion, wherein: the distal end portion includes a blade surface, the blade surface comprises: a first blade surface portion and a second blade surface portion on a front side of the distal end portion, the first and second blade surface portions intersecting each other at a ridgeline that forms a blade edge having the needle point at one end, and a third blade surface portion continuous with each of the first blade surface portion and the second blade surface portion on a proximal side of the first blade surface portion and the second blade surface portion, the third blade surface portion includes a protruding curved surface, and wherein, when a virtual plane including and extending along a center axis of the rod-like main body portion and including the needle point is established, each of the first blade surface portion and the second blade surface portion is a helical surface such that, in cross sections orthogonal to the center axis, angles between the helical surface and the virtual plane gradually and continuously decrease in a distal direction.

2. The medical puncture needle according to claim 1, wherein the protruding curved surface comprises a curved surface in which angles between the protruding curved surface and the virtual plane in cross sections orthogonal to the center axis are substantially constant.

3. The medical puncture needle according to claim 1, wherein an angular change amount of the angle per unit length in the distal direction is constant.

4. The medical puncture needle according to claim 1, wherein a straight line connecting the needle point with a point on the third blade surface portion is inclined at an angle greater than 12 degrees and less than or equal to 18 degrees with respect to the center axis, in the virtual plane.

5. The medical puncture needle according to claim 1, wherein:
the blade surface includes a fourth blade surface portion and a fifth blade surface portion formed on a back side of the distal end portion, and
the fourth blade surface portion and the fifth blade surface portion intersect each other at a second ridgeline that forms a second blade edge having the needle point at one end.

6. The medical puncture needle according to claim 1, wherein:
the first blade surface portion is symmetrical with respect to the second blade surface portion over the virtual plane.

7. The medical puncture needle according to claim 1, wherein the protruding curved surface comprises a curved surface in which angles between the protruding curved surface and the virtual plane in cross sections orthogonal to the center axis gradually decrease in the distal direction.

8. The medical puncture needle according to claim 7, wherein an angular change amount of the angle per unit length in the distal direction is constant.

9. The medical puncture needle according to claim 7, wherein:
the blade surface includes a fourth blade surface portion and a fifth blade surface portion on a back side of the distal end portion, and
the fourth blade surface portion and the fifth blade surface portion intersect at a second ridgeline that forms a second blade edge having the needle point at one end.

10. The medical puncture needle according to claim 9, wherein the first blade surface portion and the fourth blade surface portion intersect each other at a third ridgeline that forms a third blade edge having the needle point at one end, and
the second blade surface portion and the fifth blade surface portion intersect each other at a fourth ridgeline that forms a fourth blade edge having the needle point at one end.

11. The medical puncture needle according to claim 9, wherein at least one of the fourth blade surface portion and the fifth blade surface portion comprises a curved surface in which an angle with respect to the virtual plane in a cross section orthogonal to the center axis gradually increases in the distal direction.

12. A medical puncture needle comprising: a main body portion having an oval cross sectional outline defined by a major axis and a minor axis; and a distal end portion continuous with the main body portion and including a needle point, wherein: the distal end portion includes a blade surface, the blade surface comprises a first blade surface portion and a second blade surface portion intersecting at a ridgeline that forms a blade edge having the needle point at one end, and wherein, when a virtual plane including extending along a center axis of the main body portion and including the needle point is established, each of the first blade surface portion and the second blade surface portion is a helical surface such that, in cross sections orthogonal to the center axis, angles between the helical surface and the virtual plane gradually and continuously decrease in a distal direction.

* * * * *

UNITED STATES PATENT AND TRADEMARK OFFICE
CERTIFICATE OF CORRECTION

PATENT NO. : 10,772,660 B2
APPLICATION NO. : 15/883674
DATED : September 15, 2020
INVENTOR(S) : Ueda Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*